United States Patent [19]

Pope, deceased et al.

[11] Patent Number: 4,852,029
[45] Date of Patent: Jul. 25, 1989

[54] AUTOMATED MATERIAL CLASSIFICATION APPARATUS AND METHOD

[75] Inventors: Thomas A. Pope, deceased, late of Lawrenceville, Va., by Idella Pope, legal representative; Walter B. Wallin, Princeton, W. Va.; Mitchell R. Cutrell, Lawrenceville; James J. Melton, Richmond, both of Va.

[73] Assignee: Accu-Tech Incorporated, Dolphin, Va.

[21] Appl. No.: 64,072

[22] Filed: Jun. 17, 1987

[51] Int. Cl.$^4$ .................. G01N 3/20; G06F 15/46
[52] U.S. Cl. .................. 364/556; 364/506; 364/474.01; 209/521; 73/852
[58] Field of Search ............... 364/475, 506, 508, 556; 209/509, 517, 518, 519, 520, 521; 73/808, 812, 849, 852; 83/71-73, 154, 371; 144/356-357; 156/64

[56] References Cited

U.S. PATENT DOCUMENTS

| | | |
|---|---|---|
| 2,593,732 | 3/1961 | Dahlman .................. 209/587 |
| 3,029,943 | 4/1962 | Diamond et al. .......... 209/586 |
| 3,120,861 | 2/1964 | Finlay et al. ............. 209/586 |
| 3,196,672 | 7/1965 | Keller ..................... 209/587 |
| 3,345,861 | 10/1967 | Heath ..................... 73/862 |
| 3,350,687 | 10/1967 | Gabrielson et al. ....... 340/146.1 |
| 3,497,084 | 2/1970 | Murrah . |
| 3,502,123 | 3/1970 | Golick et al. ............. 209/587 |
| 3,513,690 | 10/1979 | Pellerin .................... 73/151 |
| 3,531,983 | 11/1979 | Heath et al. .............. 73/862 |
| 3,541,513 | 11/1970 | Paterson ................... 340/172.5 |
| 3,559,177 | 1/1971 | Benson ..................... 340/172.5 |
| 3,561,584 | 2/1971 | Sinyavsky et al. ........ 198/107 |
| 3,629,859 | 3/1971 | Copland et al. ........... 340/172.5 |
| 3,744,299 | 7/1973 | Bliss ........................ 73/866 |
| 3,760,636 | 9/1973 | Serry ....................... 73/852 |
| 3,788,466 | 1/1974 | Wilson et al. ............. 209/79 |
| 3,805,156 | 3/1974 | Norton et al. ............. 324/61 R |
| 3,824,851 | 7/1974 | Hagar et al. .............. 73/151 |
| 3,877,294 | 2/1975 | Shaw ....................... 73/867 |
| 3,921,152 | 4/1979 | Hagar et al. .............. 340/172.5 |
| 3,999,046 | 12/1976 | Porter ...................... 364/556 |
| 4,059,988 | 11/1977 | Shaw ....................... 73/867 |
| 4,069,851 | 1/1978 | Bibler ...................... 144/312 |
| 4,123,702 | 4/1979 | Kinanen et al. . |
| 4,166,541 | 9/1979 | Smith, Jr. ................. 209/587 |
| 4,185,672 | 1/1980 | Vit et al. .................. 144/312 |
| 4,195,346 | 3/1980 | Schroder .................. 364/475 |
| 4,201,093 | 5/1980 | Logan ...................... 73/609 |
| 4,207,472 | 6/1980 | Idelsohn et al. .......... 250/563 |

(List continued on next page.)

OTHER PUBLICATIONS

*Using a Microprocessor: A Real-Life Application Part 1—Hardware*, Computer Design, Sep. 1975, pp. 69-77 (Logan et al.).

(List continued on next page.)

*Primary Examiner*—Parshotam S. Lall
*Assistant Examiner*—Ellis B. Ramirez
*Attorney, Agent, or Firm*—Willian Brinks Olds Hofer Gilson & Lione Ltd.

[57] ABSTRACT

An automated method and apparatus for grading pre-cut lumber products according to selected physical properties thereof such as modulus of elasticity (MOE) and modulus of rupture (MOR) are disclosed. A conveyor transports boards to be graded to an automated lumber feeding mechanism which sequentially rotates each board from a loading to a grading position. In the grading position, an impactor impacts one longitudinal end of the board to generate a compression force and a detector at the opposite longitudinal end converts the compression force to an electrical signal. Data acquisition circuitry samples and stores at least one cycle of the signal and a computer analyzes the samples and assigns values to predetermined parameters which characterize the signal. The computer utilizes the parameter values in one or more predetermined formulas which are optimum statistical predictors of the selected physical properties as a function of the parameters to obtain values for the selected physical parameters. The computer assigns a grade classification to each board according to the grading criteria based upon the calculated values of the physical parameters and a marking mechanism applies appropriate grade indicia to the board.

66 Claims, 19 Drawing Sheets

U.S. PATENT DOCUMENTS

| | | |
|---|---|---|
| 4,221,974 | 7/1981 | Mueller et al. |
| 4,262,793 | 4/1981 | Hebenstreit et al. |
| 4,269,303 | 5/1981 | Cornell ................................ 198/680 |
| 4,280,185 | 7/1989 | Martin ................................. 364/506 |
| 4,283,629 | 8/1981 | Habermehl et al. ............ 250/445 T |
| 4,299,326 | 11/1981 | Ulch .................................... 209/564 |
| 4,313,348 | 2/1982 | Madsen ................................ 73/852 |
| 4,321,834 | 3/1982 | Oliver .................................. 73/812 |
| 4,358,009 | 11/1982 | Rysti ................................... 209/517 |
| 4,366,712 | 1/1983 | Bathmann et al. .................... 73/600 |
| 4,377,238 | 3/1983 | Wilks et al. ......................... 209/587 |
| 4,392,204 | 8/1983 | Prim et al. |
| 4,399,701 | 8/1983 | Dunlop ................................. 73/579 |
| 4,450,727 | 5/1984 | Reinholm et al. .................... 73/862 |
| 4,476,755 | 10/1984 | Hedin .................................. 83/364 |
| 4,500,835 | 2/1985 | Heikkila ......................... 324/585 R |
| 4,611,304 | 9/1986 | Butenko et al. ..................... 364/571 |
| 4,638,440 | 1/1987 | Brough et al. ...................... 364/475 |
| 4,708,020 | 11/1987 | Lau et al. ............................ 374/142 |

OTHER PUBLICATIONS

*Using a Microprocessor: A Real-Life Application Part 2—Software,* Computer Design, Oct. 1975, pp. 81–89 (Cannon et al.).

*Background to Machine Stress Grading,* Forest Products Journal, vol. 18, No. 4, Apr. 1968, pp. 87–97 (Hoyle).

*Proceedings of the Symposium on Nondestructive Testing of Wood,* Mar. 1964, Advertisement and Price List for MOD-E-LAS, Porter Engineering Limited, 576 Cedarbridge Way, Richmond, B.C., Canada, May, 1972.

*A Vibrational Approach to . . . NonDesctructive Testing of Structural Lumber,* Forest Products Journal, vol. XV, No. 3, Mar. 1965, pp. 93–101 (Pellerin).

*Slope-of-Grain Indicator,* May 1973, pp. 50–54 (McLauchlan et al.).

*Textbook of Wood Technology,* McGraw Hill Book Co., Inc., New York, N.Y., 1952, pp. 127–153 (Brown et al.).

*Ultrasonics for Wood Industries,* Oregon Forest Research Center, Forest Products Research Report No. E-2, Apr. 1960, pp. 23–24 (Morris).

*Stress Waves Produce Lumber Strength Data,* Forest Industries, Mar. 1986, pp. 32–33 (DeBonis).

*Stress Wave Attenuation as an Indicator of Lumber Strength,* Forest Products Journal, vol. 27, No. 6, Jun. 1977, pp. 39–43 (Kaiserlik et al.).

*Machine Stress Rating of White Spruce Joists,* Information Report OP-X-54, Study Number OP-055, Department of the Environment, Canadian Forestry Service, Nov. 1972 (Jessome).

*Non-Destructive Testing of Cross-Arms for Strength,* Canadian Department of Forestry Publication No. 1021, 1963 (Miller).

*Electronic Selection of Structural Wood Members for Furniture Manufacture,* Annual Meeting of the National Association of Furniture Manufacturers, Louisville, Ky., Sep. 14, 1968 (Marra et al.).

*Machine Stress-Rating Capacity Triples Over Past Three Years,* Forest Industries, Jan. 1980, pp. 45–47 (Logan).

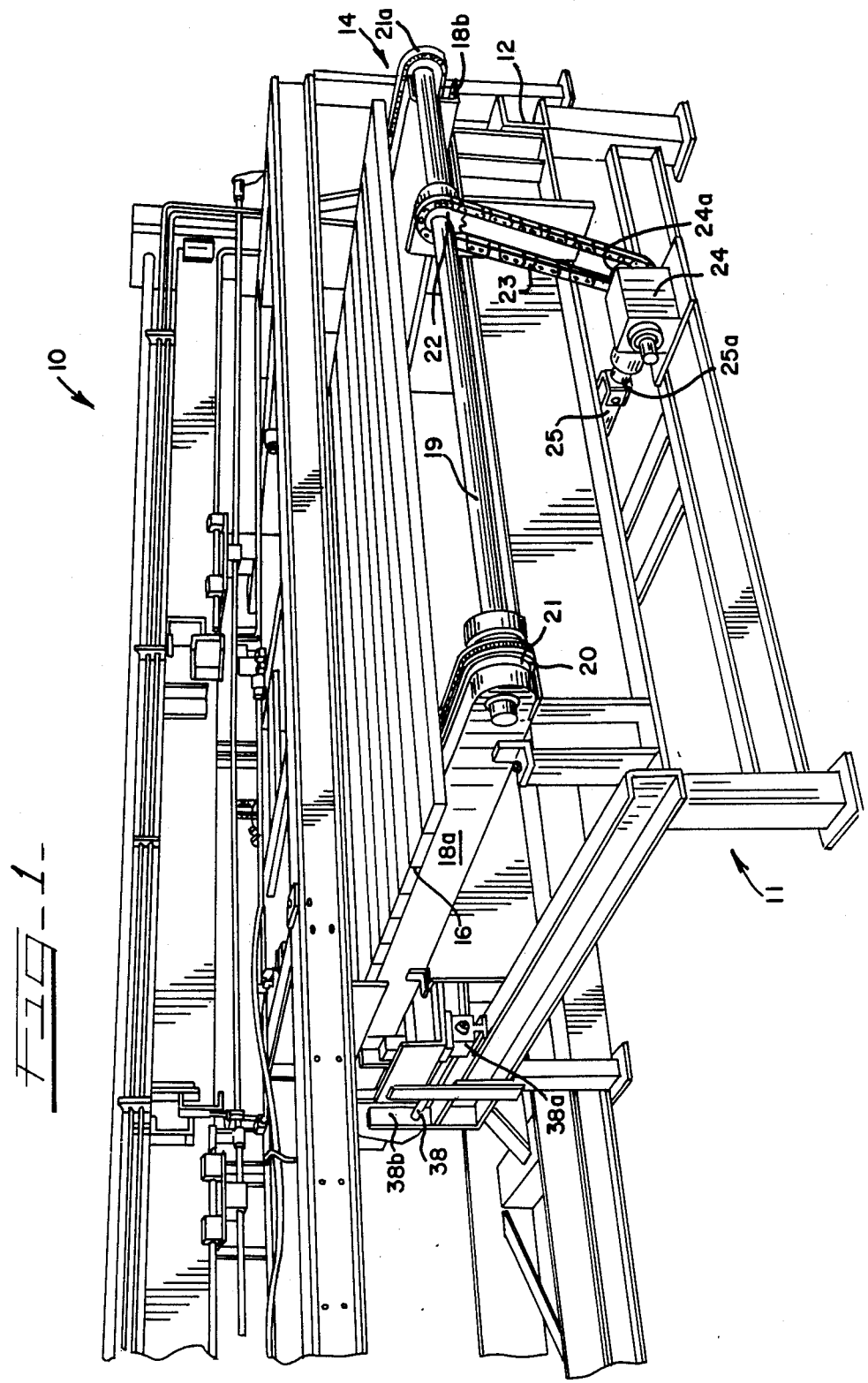

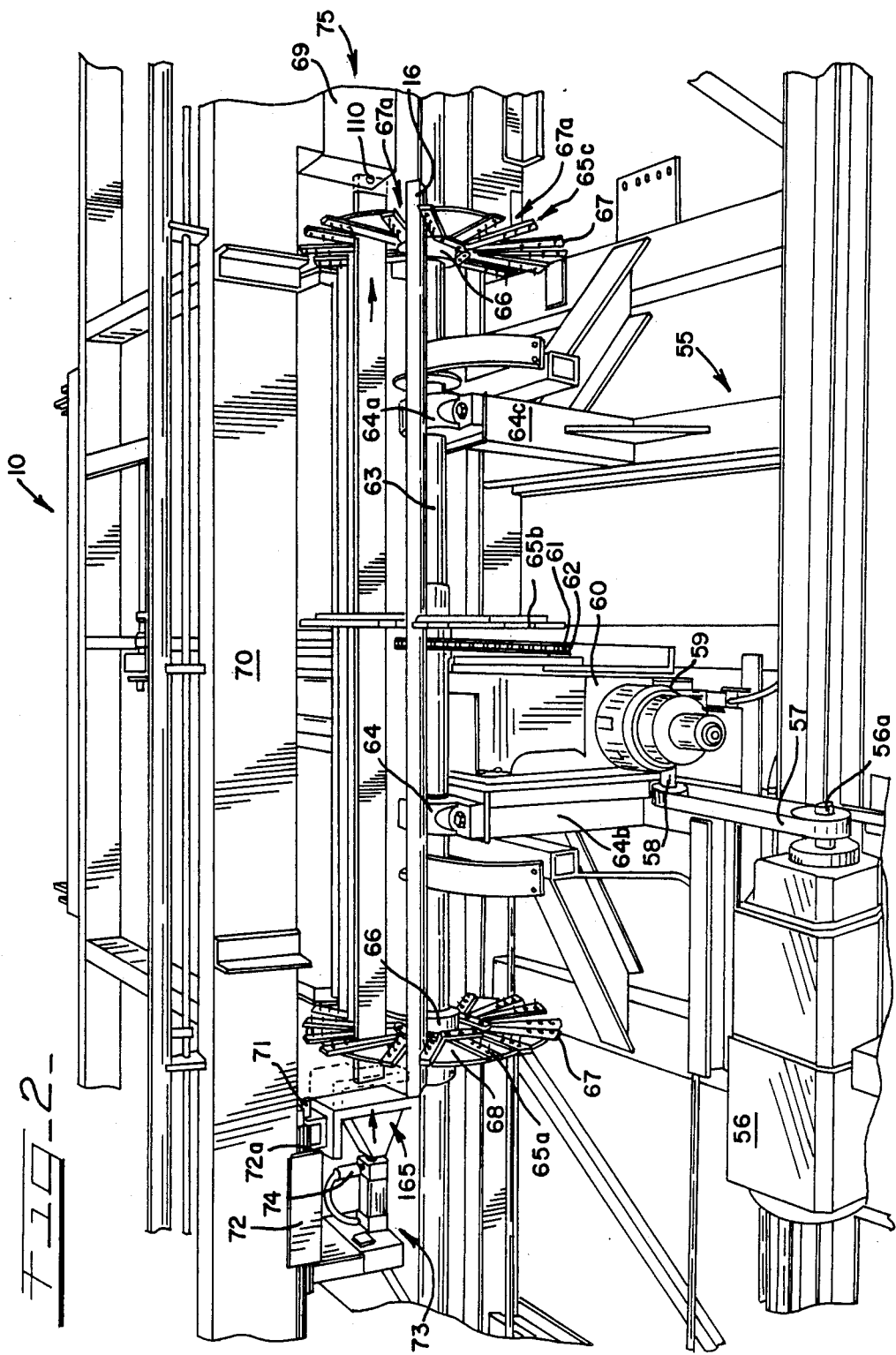

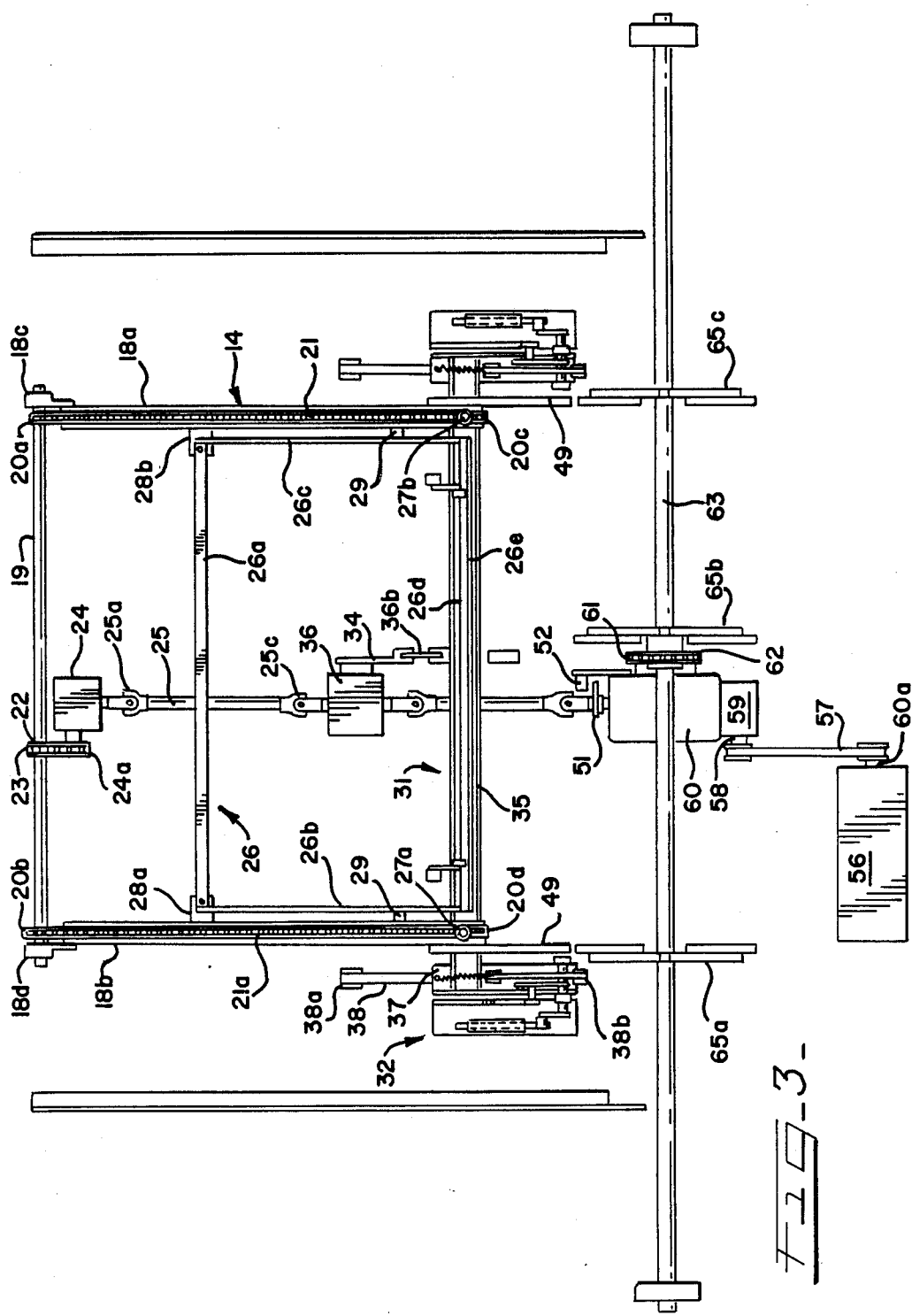

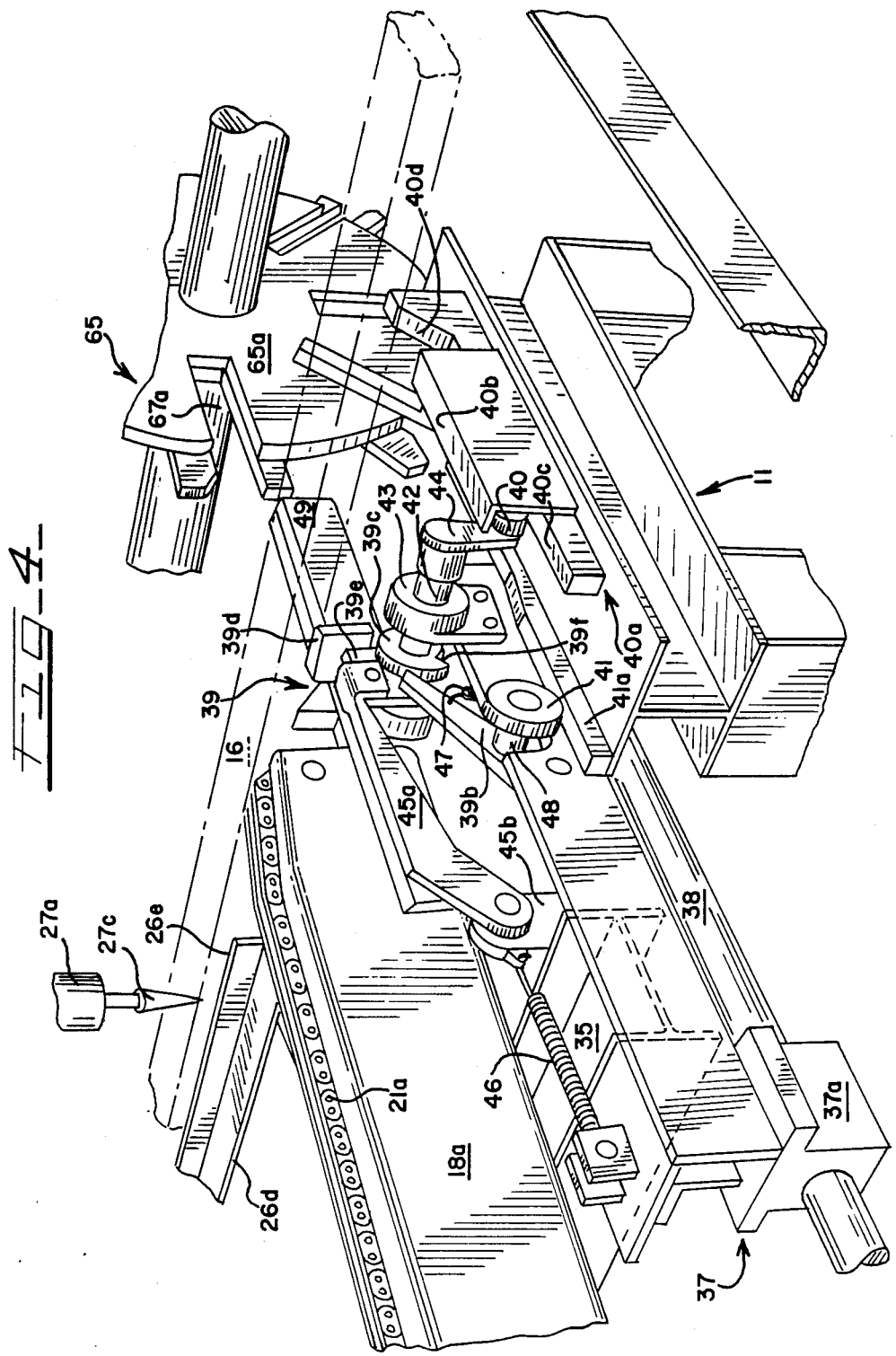

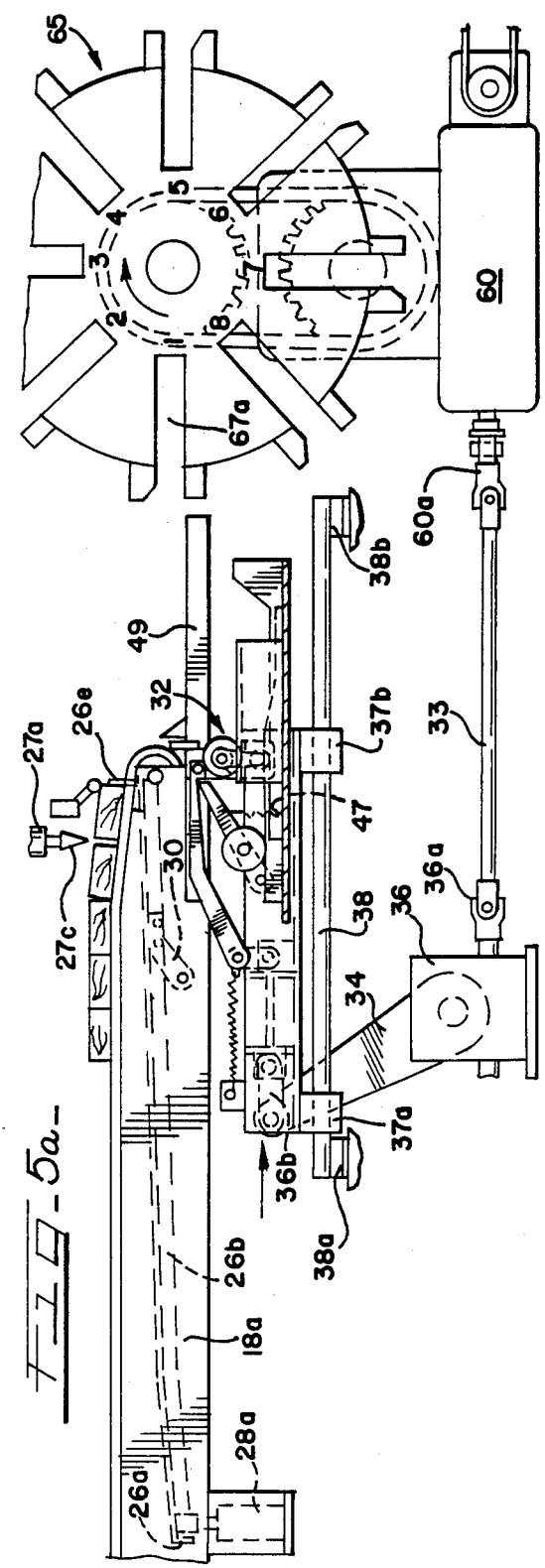
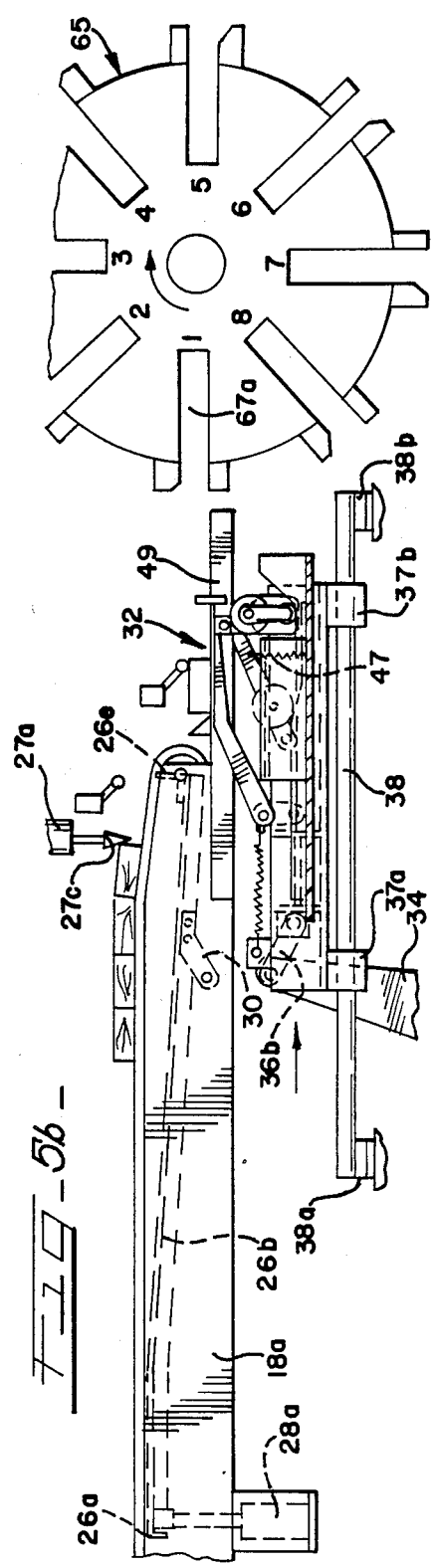

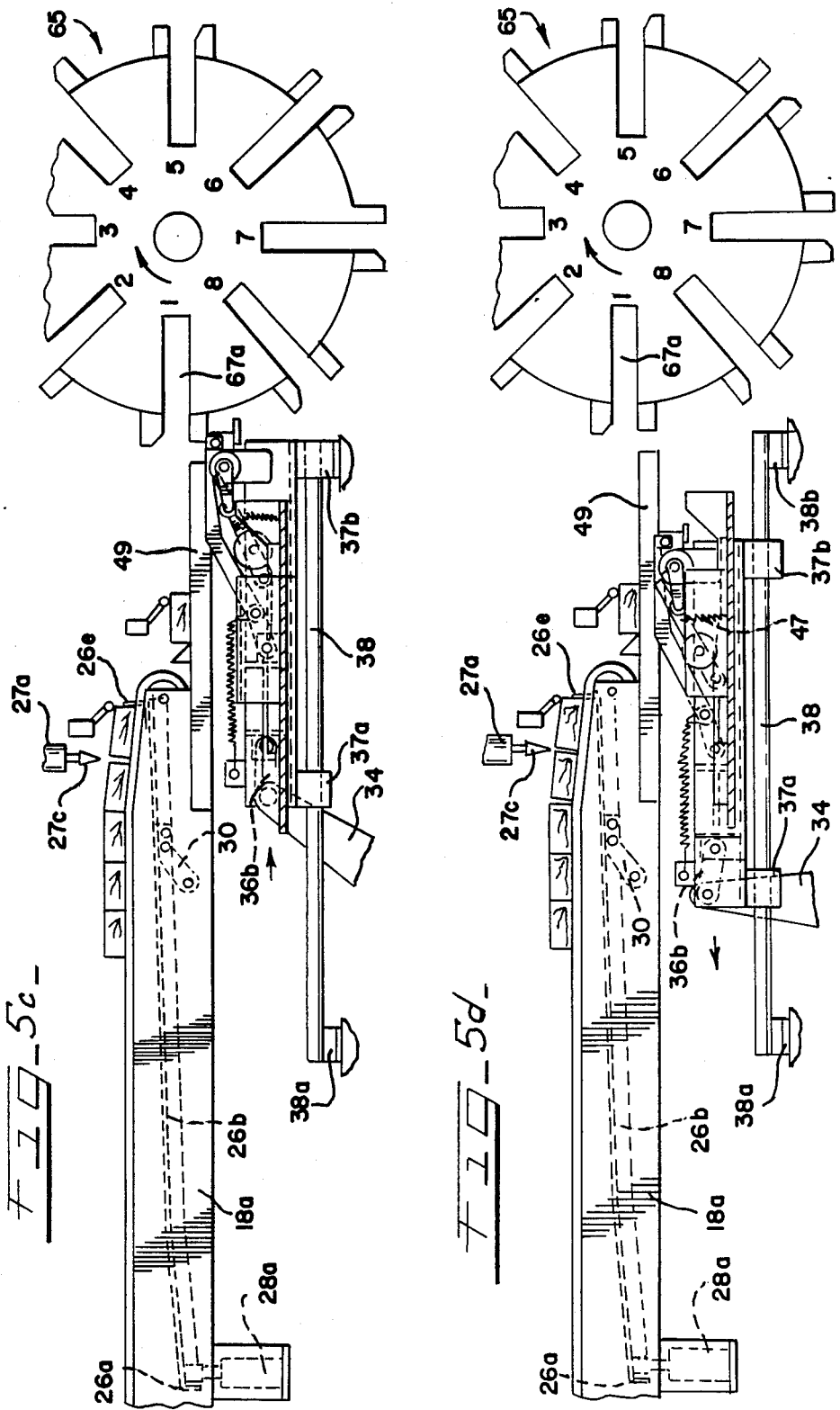

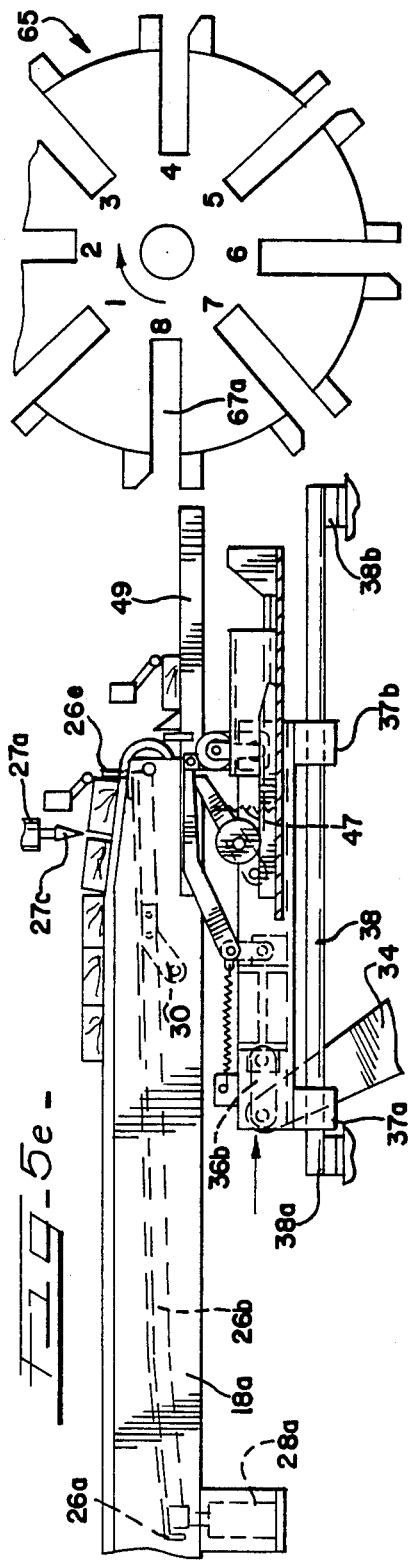
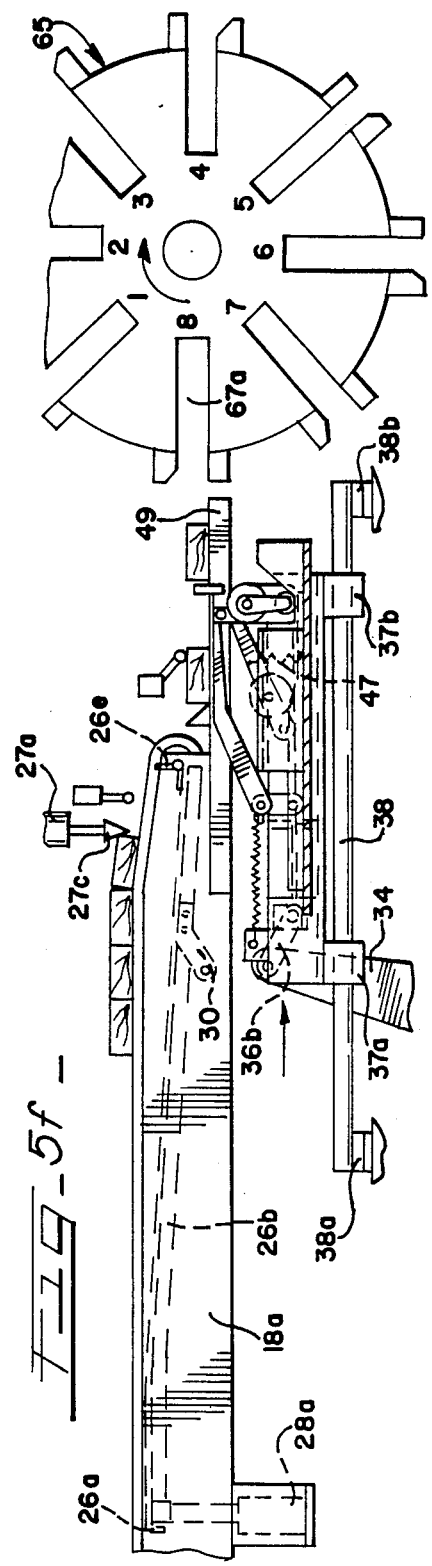

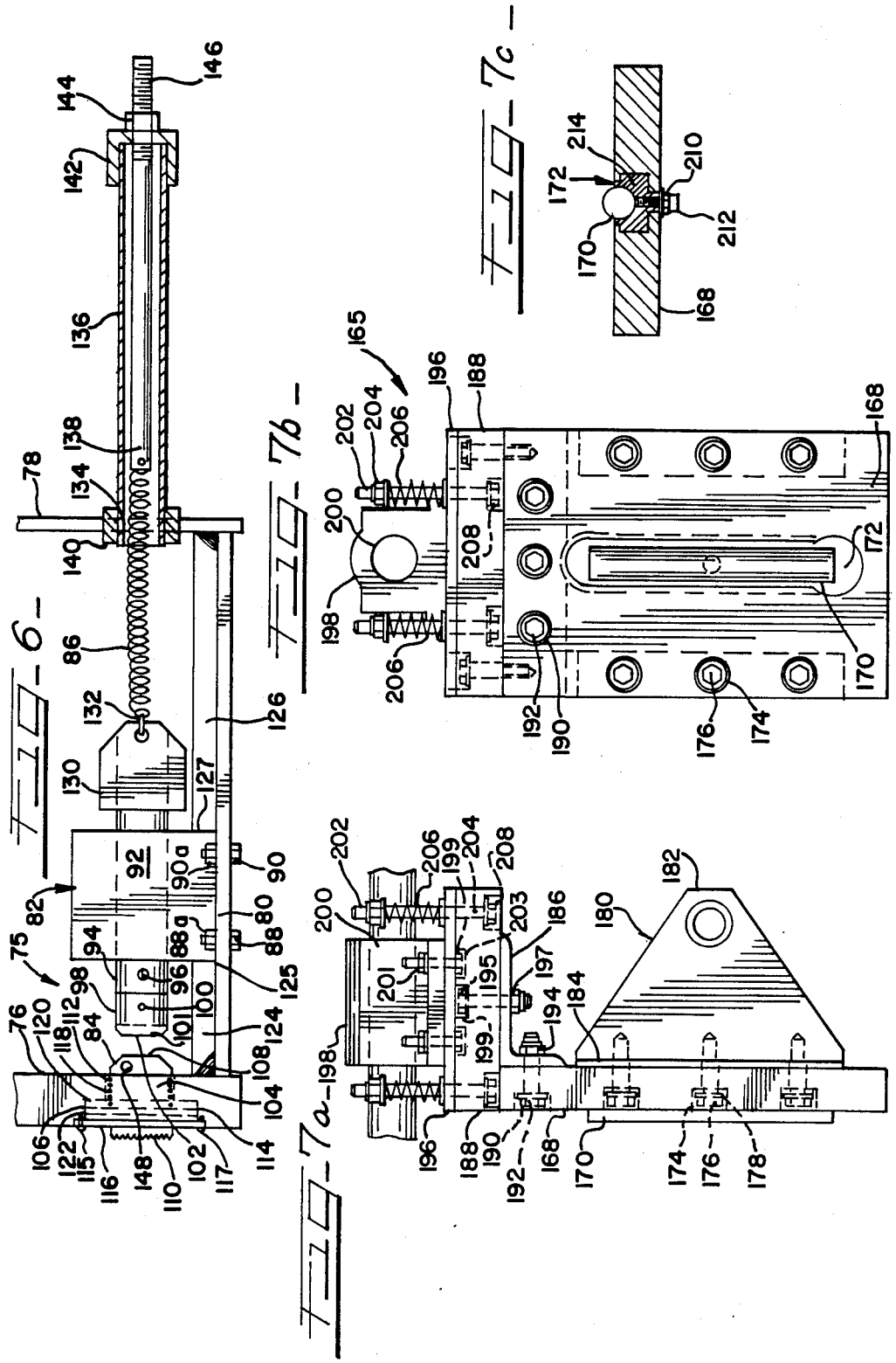

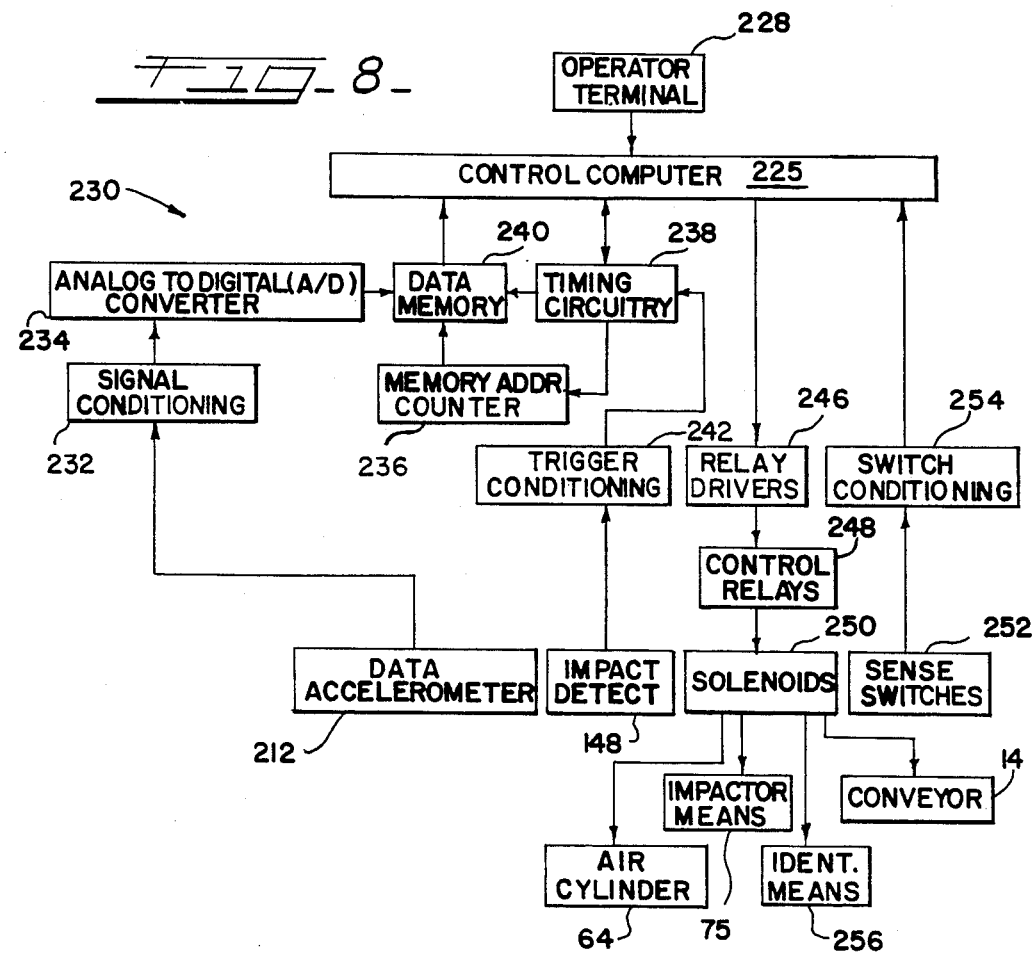
FIG_8_
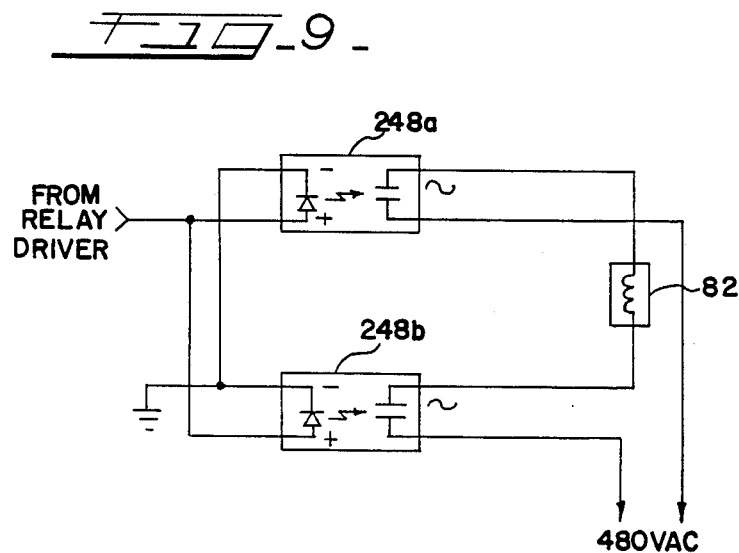
FIG_9_

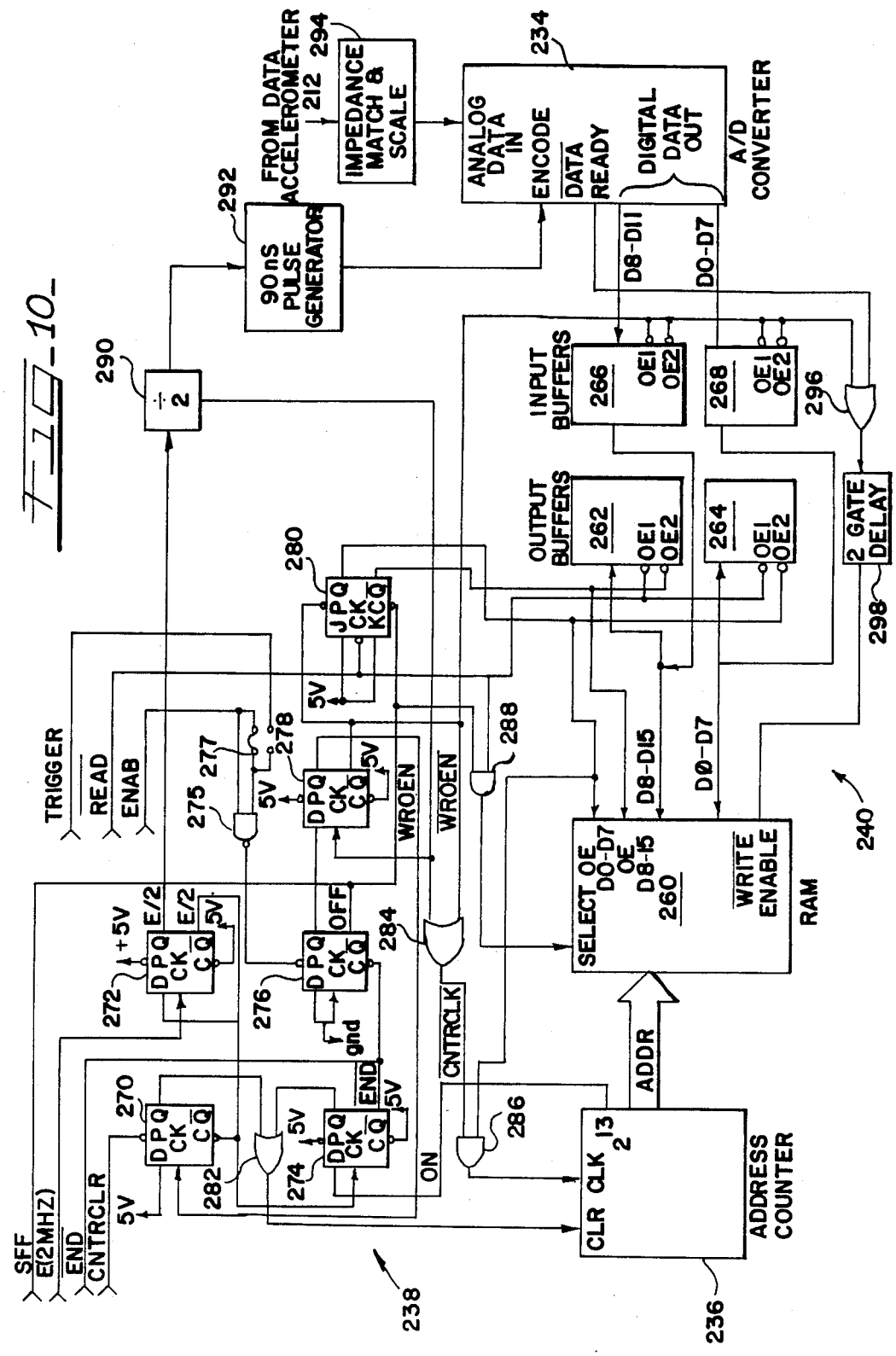
FIG_10

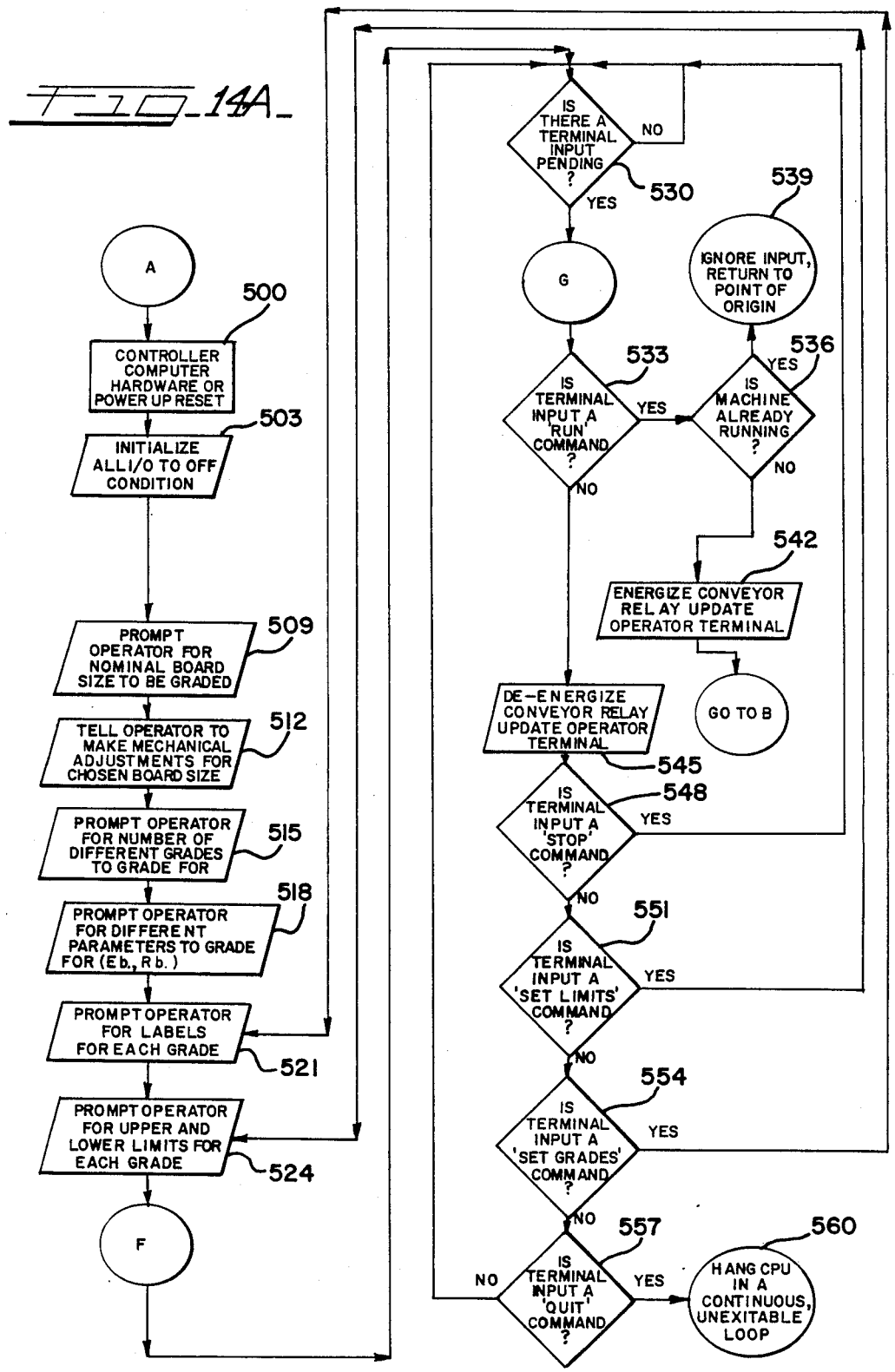

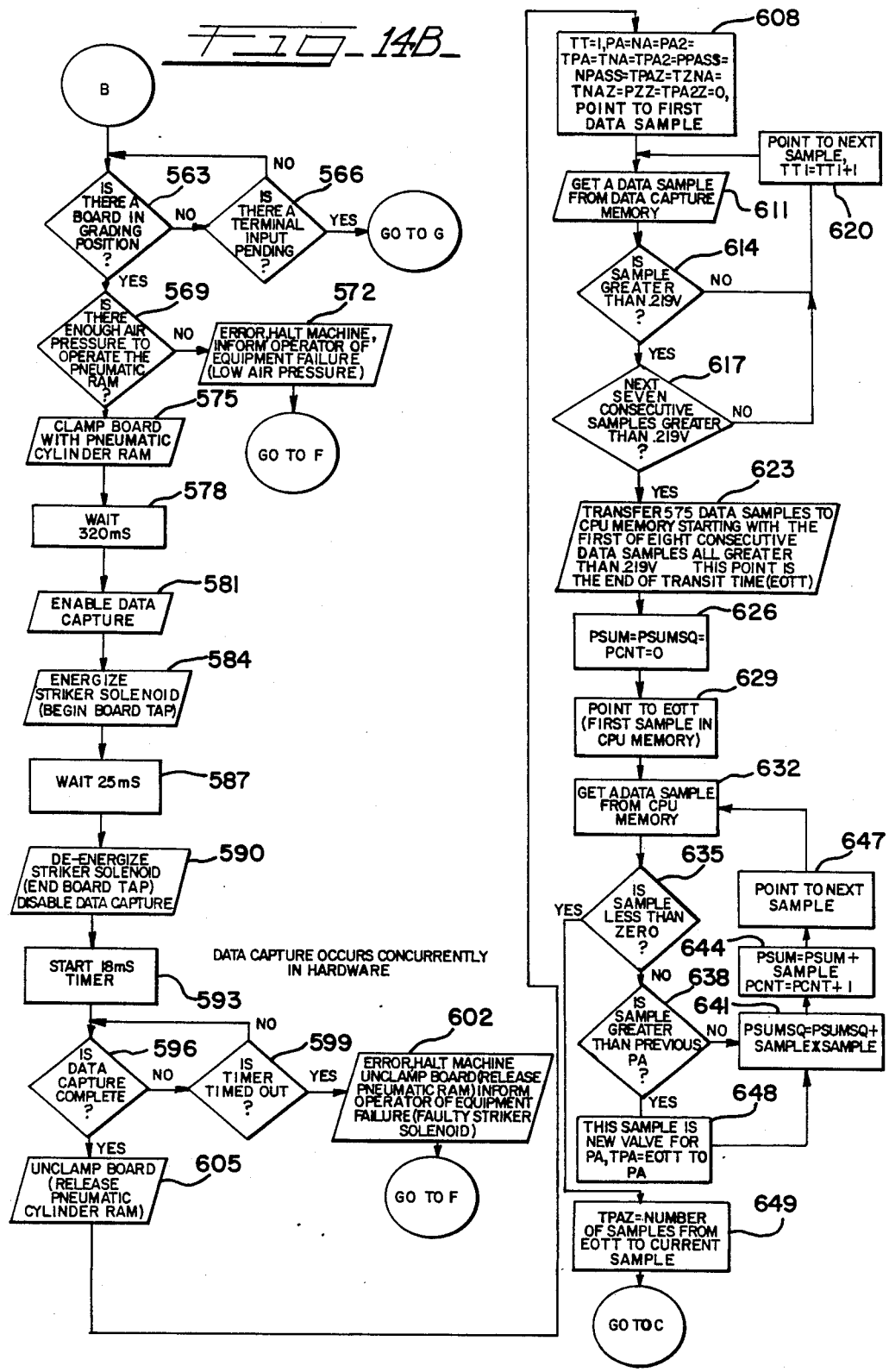

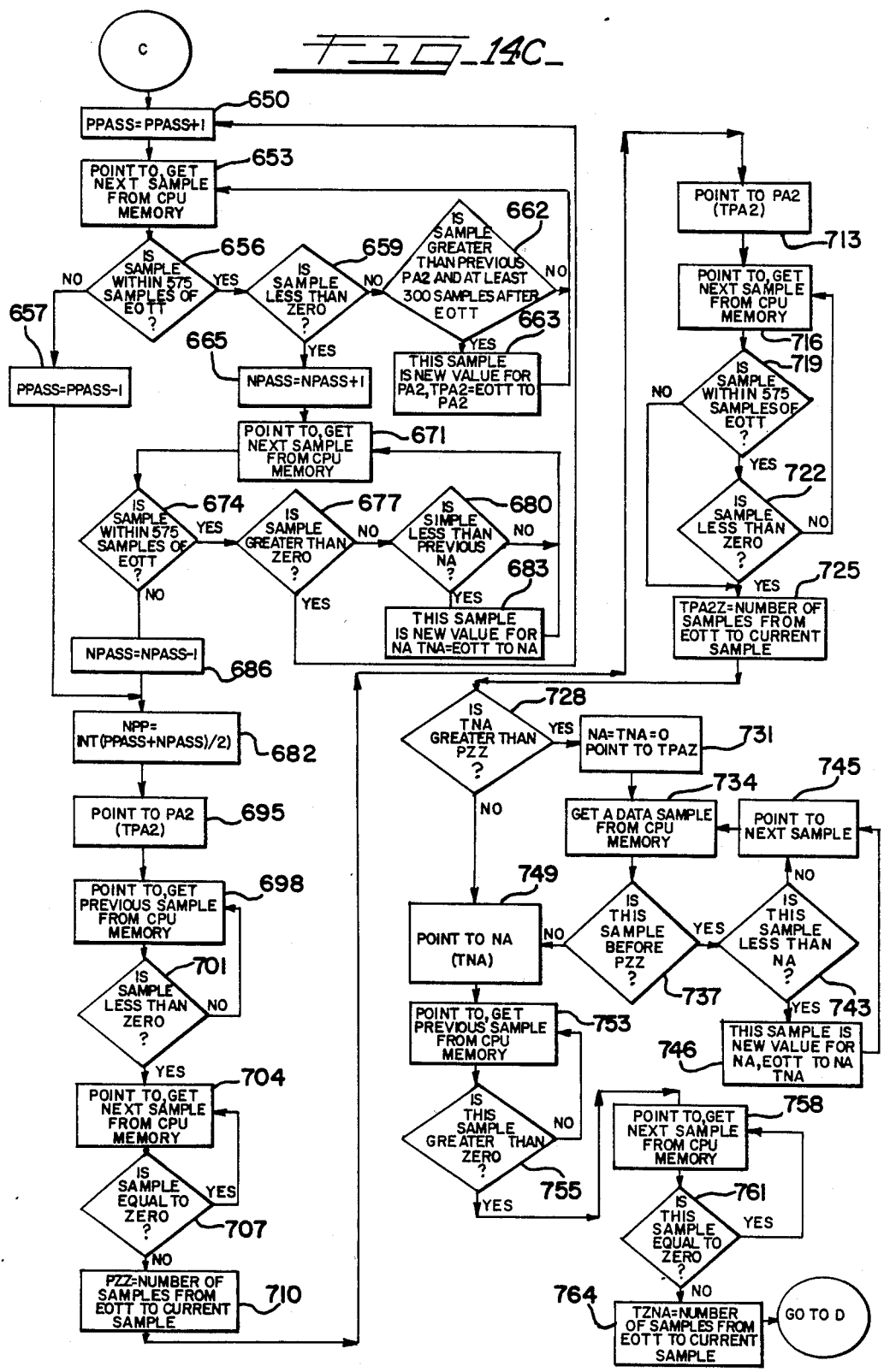

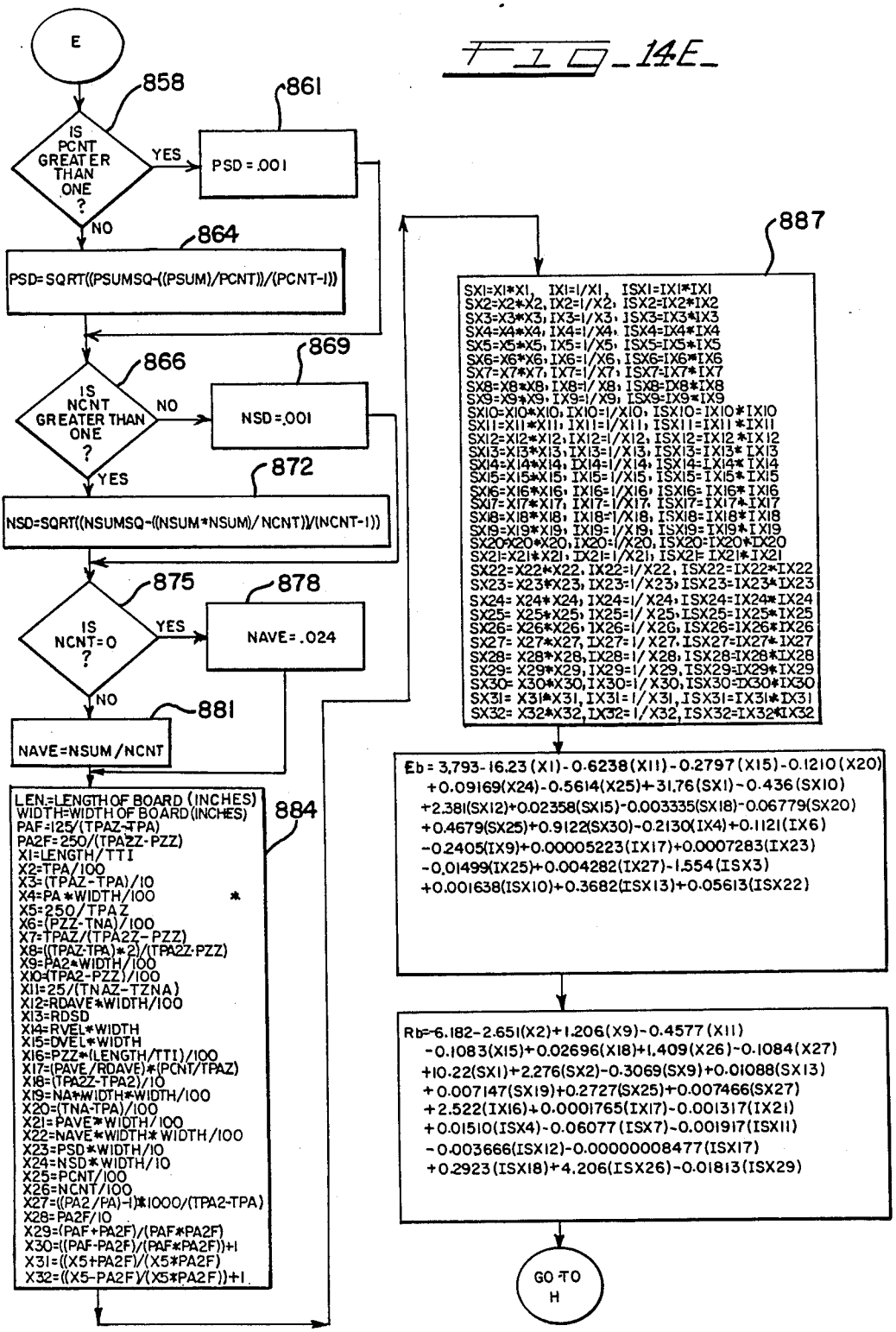
FIG_14E

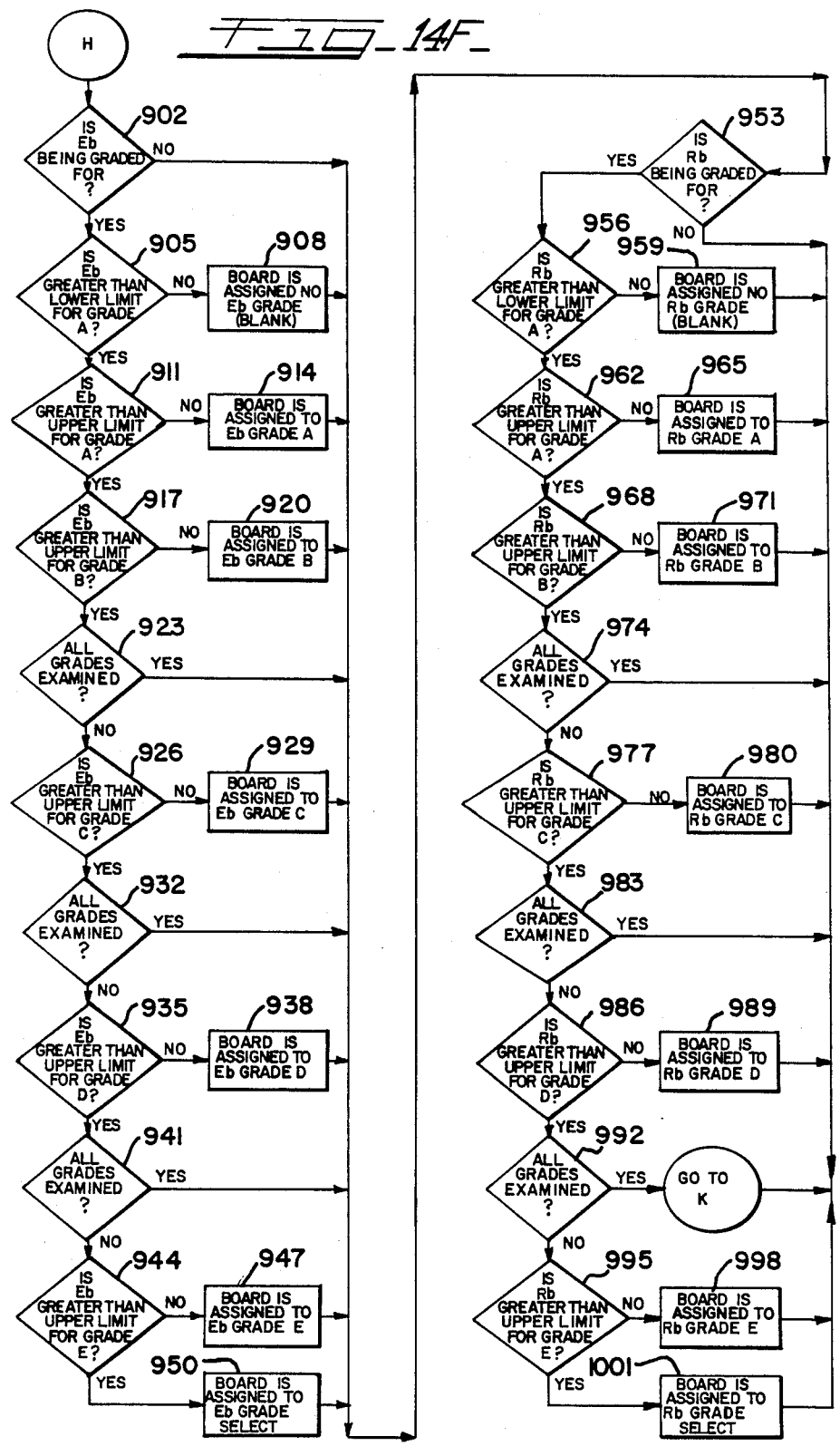
FIG_14F

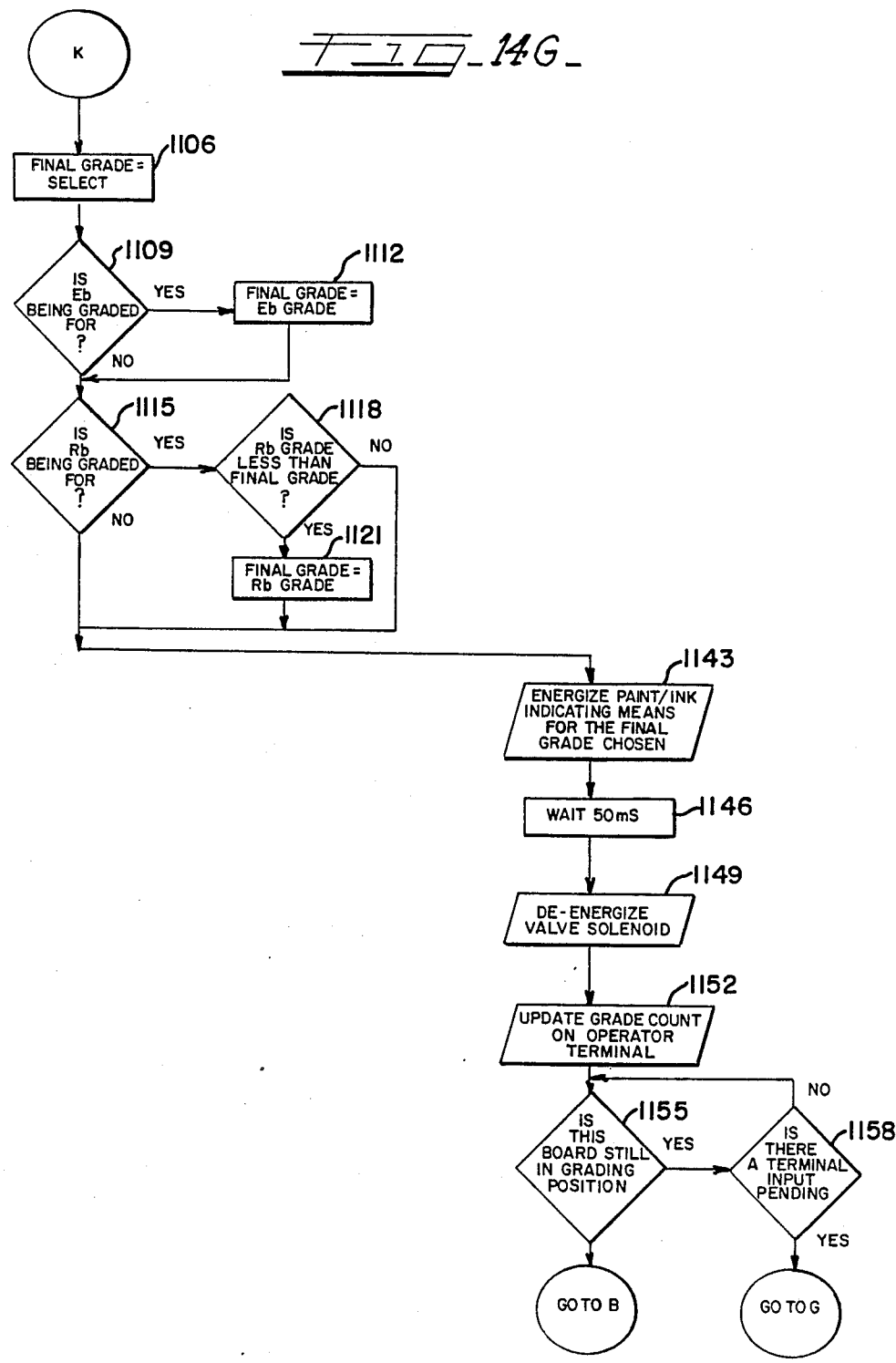
FIG_14G_

AUTOMATED MATERIAL CLASSIFICATION APPARATUS AND METHOD

BACKGROUND OF THE INVENTION

1. Field of the Invention

This invention relates generally to apparatus and methods for measuring certain properties of energy-absorbing materials such as wood products, including wood-adhesive composite products, and metals, plastic, and concrete products. More specifically, the invention relates to an automated apparatus and method for measuring stiffness, or modulus of elasticity (MOE), and strength, or maximum stress at failure (MOR), of wood and related products, and for identifying such products in conjunction with measured values of parameters developed by the invention.

2. Description of Prior Art

Typically, the market value of wood products, such as pre-cut lumber products, is determined by classifying or grading the products according to established grading rules and procedures. In the mid-1920's, visual grading criteria were adopted for grading wood products in terms of their engineering properties, such as elasticity and strength under flexure, tension, and compression. The criteria adopted have come to be known as Visual Stress Grading Rules. The Visual Stress Grading Rules, which are widely used throughout the United States, are based on the visual inspection of wood products for certain predetermined, visually observable characteristics such as knots, warp, and the like. Under the Visual Grading Rules, trained operators or graders visually inspect the wood products and assign grade classifications thereto based on their judgment concerning the engineering properties of the products as a function of the visual criteria. The grades assigned by the operators are verified statistically by reference to past structural experience and laboratory testing of similar products.

In the 1960's, the first lumber grading machines designed to mechanically test individual pieces of pre-cut lumber non-destructively in flexure were introduced. The process of automatically grading individual pieces of lumber non-destructively in flexure by machine has become known as Machine Stress Rating (MSR) and lumber graded by such machines is commonly referred to as MSR lumber. Presently, there are estimated to be between 20 and 30 MSR grading installations in the United States. Unlike visually graded products, lumber grading machines typically grade MSR products automatically by actually measuring a selected parameter of the products under flexure, such as resistance to flexure, and relating the parameter to a selected engineering property. At present, structural MSR lumber is classified on the basis of a single measured parameter: stiffness in flexure or modulus of elasticity (MOE). From the measured MOE, strength values, e.g., modulus of rupture (MOR), are often assigned in accordance with a statistical correlation between stiffness and strength for similar destructively tested lumber samples.

Other prior art grading or classification machines have also been developed. Such machines operate on a variety of principles including inducing and measuring RF or microwave energy signals in the lumber and inducing stress waves and measuring the velocity or acceleration thereof. Similarly to the known MSR machines, these machines do not individually calculate selected physical parameters such as MOE and MOR directly and independently for each piece of lumber. In addition, such machines are typically not suitable for use in applications requiring high speed operation such as in the production line of a typical lumber mill.

The present invention seeks to provide an automated material classification apparatus and method for speedily and accurately determining selected physical parameters or properties of wood products particularly, and of other energy absorbing materials such as plastic, concrete, and metal, in general.

A significant feature and advantage of the apparatus and method of the invention is the ability to accurately calculate multiple selected physical parameters or properties of the material to be classified (such as MOE and MOR) individually and independently for each and every piece of the material.

Another significant feature and advantage of the apparatus and method of the invention is the ability to individually test each piece of material, analyze the results, and calculate the selected physical parameters at sufficiently high rates of speed to enable operation of the invention in the production line of a typical lumber mill.

Still another significant feature and advantage of the apparatus and method of the invention is the ability to test and classify the material without subjecting the material to physical deformation which may result in structural damage.

Other significant features and advantages are also provided and will become apparent from the detailed description and illustration of a presently preferred embodiment of the automated material classification apparatus and method set forth below.

SUMMARY OF THE INVENTION

The foregoing and other features and advantages are obtained by providing an automated material classification apparatus which includes a device for impacting a piece of material to generate a compression force therein, and a detector for providing a signal related to the generated force. Also provided is a computing facility for assigning values to a selected plurality of predetermined parameters characterizing at least one cycle of the signal correspondig to the generated force. The computing facility processes the selected predetermined parameters according to at least one predetermined formula which relates the parameters to at least one selected physical parameter of the material and generates at least one value signal corresponding to the physical parameter. An identifying apparatus is provided for receiving the value signal and for operating to provide classification indicia associated with the calculated parameter.

According to another aspect of the invention, an automated feeding apparatus is provided. The feeding apparatus includes a rotatable lumber receiving mechanism having a loading position and a processing position associated therewith. A conveyor is provided for continuously transporting pieces of lumber to the loading position of the receiving mechanism. A restraining apparatus selectively restrains pieces of lumber from entering the receiving mechanism. A control is provided for controlling the restraining means to release individual pieces of lumber to be loaded into the lumber receiving mechanism, and a drive is provided for rotating the receiving mechanism so that each piece of lumber held therein is rotated from the loading to the processing position.

According to yet another aspect of the invention, an automated data acquisition apparatus is provided. The data acquisition apparatus includes a data source that generates a data signal related to a condition of interest and a data acquisition signal indicative of the occurrence of the condition of interest. Also included are a data storage, circuitry responsive to the data acquisition signal for sampling the data signal and storing the samples in the data storage, and circuitry for signalling a central data processor when a predetermined number of samples have been stored.

BRIEF DESCRIPTION OF THE DRAWINGS

The features which are believed to be characteristic of the present invention are set forth in the appended claims. The invention itself, together with the above-identified and other features and advantages thereof, will become apparent from the following detailed description of a presently preferred embodiment, taken in conjunction with the drawings, in which:

FIG. 1 is a perspective view of the in-feed side of a preferred automated lumber classification apparatus;

FIG. 2 is a perspective view of the discharge side of the automated lumber classification apparatus of FIG. 1;

FIG. 3 is a top plan view of the automated lumber classification apparatus of FIGS. 1 and 2;

FIG. 4 is an enlarged partial perspective view showing lumber restraining and loading means of the automated lumber apparatus illustrated in FIG. 3;

FIGS. 5a through 5f are side elevation views of the lumber restraining and loading means shown in FIG. 4 illustrating the sequence of operation of the restraining and loading means;

FIG. 6 is a side elevation view in section of preferred impactor means of the apparatus shown in FIG. 2, illustrating the details thereof;

FIG. 7a is a side elevation view of preferred detector means of the apparatus shown in FIG. 2, illustrating the details thereof;

FIG. 7b is a front elevation view of the detector means of FIG. 7a;

FIG. 7c is a top plan view of the front plate of the detector means of FIG. 7a, illustrating the assembly of a pickup rod and accelerometer of the preferred detector means;

FIG. 8 is a block diagram illustrating generally the electronic control and processing elements of the preferred apparatus;

FIG. 9 is a schematic diagram illustrating the details of the control relays for the hammer solenoid of the impactor means shown generally in FIG. 8;

FIG. 10 is a schematic and block diagram illustrating the details of the data acquisition circuitry shown generally in FIG. 8;

FIGS. 14a through 14g are flow charts illustrating in detail the operation and control of the preferred lumber classification apparatus.

DETAILED DESCRIPTION OF THE PRESENTLY PREFERRED EMBODIMENT

Figure 11:
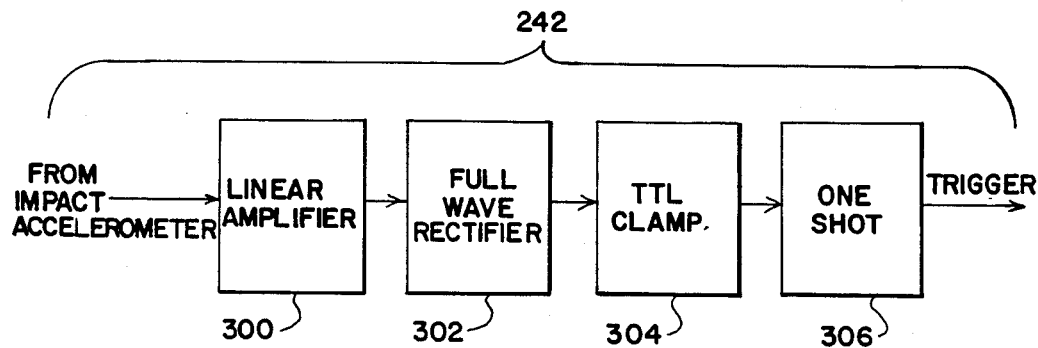
FIG. 11 is a block diagram illustrating in greater detail the trigger conditioning circuit illustrated generally in FIG. 8.

The detailed description of the presently preferred embodiment of the invention is set forth below in terms of an apparatus and method for classifying pre-cut wood products in terms of stiffness (MOE) and strength (MOR) in flexure. It is understood that this description is exemplary and that the principles of the invention have broad application to automated classification of other energy-absorbing materials such as plywood, wood composites, and other wood products, concrete, plastic, and the like as well. It is also understood that the principles of the invention are equally applicable to the classification of wood or other energy absorbing materials by other selected physical properties such as stiffness and strength in tension or compression, for example.

Referring to the drawings, FIGS. 1 and 3 illustrate the in-feed side of an automated lumber classification apparatus 10 embodying the principles of the invention. The in-feed side includes a frame 11 on which is mounted a horizontal conveyor 14. The conveyor 14 is designed to support individual pieces of pre-cut lumber or boards 16 length-wise and to transport the pieces of lumber or boards 16 into the apparatus 10 for classification. The conveyor 14 is comprised of a pair of elongated horizontal frame sections 18a and 18b which extend in parallel into proximity with a rotatable lumber receiving means within the apparatus 10, which is described in detail below. The frames 18a and 18b have bearing rings 18c and 18d respectively mounted in alignment near the respective in-feed ends thereof. A cylindrical drive rod 19 is rotatably supported at its opposite ends horizontally within the bearing rings. A pair of short, horizontal rods are rotatably mounted in a second set of bearing rings (not visible) near the respective discharge ends of the side frames 18a and 18b which are in proximity to the lumber receiving means mentioned above. The drive rod 19 has mounted thereon near opposite ends thereof toothed sprockets 20a and 20b. Each of the short rods near the discharge end of the conveyor 14 has a corresponding toothed sprocket 20c and 20d mounted thereon. The corresponding sprockets 20a and 20c, and 20b and 20d engage endless loop conveyor chains 21 and 21a respectively.

The drive rod 19 also has a toothed sprocket 22 mounted thereon intermediate the sprockets 20. The sprocket 22 engages one end of an endless loop drive chain 23. The other end of the drive chain 23 is engaged by a toothed sprocket 24a connected to the output shaft of a reduction gear 24, which is suitably a conventional right angle drive having a reduction of approximately 1.5 to 1. The input shaft of the reduction gear 24 is coupled by conventional universal coupling means 25a to one end of a rotatable drive shaft 25, the other end of which is coupled by conventional universal coupling means 25c to a rotatable pass-through shaft of a conventional oscillating drive 30.

As the drive shaft 25 rotates, the sprocket 24a of the reduction gear 24 rotates and drives the drive chain 23, which in turn rotates the drive rod 19 and drives the conveyor chains 21 and 21a. The conveyor chains 21 and 21a engage the pieces of lumber 16 mounted thereon near opposite longitudinal ends thereof and transport the pieces length-wise toward the rotatable lumber receiving means described in detail below.

It is understood that the principles of the invention can be carried out as described in detail below without the use of the conveyor 14. However, the conveyor 14 is a preferred element which provides means to rapidly and sequentially transport individual pieces of lumber into the apparatus 10 for grading, thus allowing the apparatus 10 to operate at the high rates of speed required for use in some environments such as the production line of a typical lumber mill. In such environments, the conveyor 14 may be directly interfaced with the discharge conveyor of cutting or weighing apparatus of the mill to provide an integrated, completely automated, high speed system. In other applications not requiring interface to a mill's discharge conveyor, lumber to be classified may be manually loaded onto the conveyor 14 at a somewhat slower rate while still retaining the advantages of having the lumber automatically queued and loaded.

FIGS. 1, 3, 4, and 5a-f illustrate lumber restraining and loading means of the preferred embodiment. The lumber restraining and loading means operate cooperatively to sequentially restrain and load individual boards from the conveyor 14 into the rotatable lumber receiving means 65 illustrated partially in FIGS. 4 and 5a-f and described in detail below. The lumber restraining means generally comprises a tiltable frame 26, a pair of pneumatic dogs 27a and 27b, and a pair of pneumatic lifters 28a and 28b. In the preferred embodiment, the frame 26 is generally rectangular. The in-feed end 26a of the frame 26 is supported at its opposite ends on the pneumatic lifters 28a and 28b respectively, which are preferably conventional pneumatic cylinders. The sides 26b and 26c of the frame 26 are pivotally connected to the inside surfaces of the horizontal frames 18a and 18b of the conveyor 14 by pivot pins or bolts 29. The pins or bolts 29 mount in corresponding openings of pivot arms 30 which are connected by bolts or other fastening means to the opposite sides 26b and 26c. The end 26d of the frame 26 is preferably located near the discharge end of the conveyor 14. The end 26d has formed therewith or bolted thereto a vertical lip piece 26e which extends the length of the end 26d.

The pneumatic dogs 27a and 27b preferably comprise conventional pneumatic cylinders having spiked ends 27c and 27d respectively formed at or mounted to the ends thereof. In the preferred embodiment, the pneumatic dogs 27a and 27b are mounted by conventional connecting means to the frame 11 directly above the conveyor chains 21 and 21a of the conveyor 14 and slightly nearer the in-feed end of the conveyor 14 than the vertical lip 26e of the end 26d of the frame 26. The cylinders and spiked ends 27c and 27d are preferably oriented vertically with the spiked ends 27c and 27d pointed downwardly toward the conveyor chains 21 and 21a.

The frame 26 is preferably mounted far enough below the level of the conveyor chains 21 and 21a to avoid interfering with movement of the lumber 16 on the conveyor 14. The frame is preferably mounted high enough so that when the lifters 28a and 28b are not activated, the frame 26 tilts upwardly toward the discharge end of the conveyor 14 as shown in FIGS. 5a, c, d, and e, and the vertical lip 26e extends above the level of the conveyor chains 21 and 21a to block or restrain the lumber on the conveyor 14 from being discharged from the conveyor 14. When the lifters 28a and 28b are activated, they extend upwardly and lift the in-feed end 26a of the frame 26. This in turn causes the sides 26b and 26c of the frame 26 to pivot on the pivot bolts 29 and the discharge end 26d of the frame 26 to tilt downwardly. When the discharge end 26d tilts downwardly, the vertical lip 26e is positioned below the level of the conveyor chains 21 and 21a and does not restrain boards on the conveyor 14 from being discharged therefrom.

The pneumatic dogs 27a and 27b are preferably positioned closer to the in-feed end of the conveyor 14 than the vertical lip 26e by approximately the width of one board 16. As shown best in FIGS. 5a-f, when the dogs are not activated the spiked ends 27c and 27d are retracted and do not restrain boards 16 on the conveyor 14. When the dogs are activated, the spiked ends thereof extend downwardly preferably far enough to wedge between the two boards closest to the discharge end of the conveyor 14 and restrain boards except for the board closest to the discharge end of the conveyor 14 from further movement.

In the preferred embodiment, the dogs 27a and 27b and the lifters 28a and 28b are controlled, i.e., are activated and deactivated together as a group by a signal from a dedicated control logic circuit. Alternately, the dogs and lifters can be controlled by signals from the control computer described in detail below. Although the lifters and dogs are preferably pneumatic devices, equivalent electrical solenoid or hydraulic devices could also be used. The control logic circuit (not shown) controls the dogs and lifters so that when the lifters 28a and 28b are activated to tilt the discharge end 26d and the vertical lip 26e of the frame 26 downwardly into the non-restraining position, the dogs 27a and 27b are activated to extend the spiked ends 27c and 27d thereof downwardly to the restraining position. Assuming that boards are on the conveyor 14 in the positions illustrated in FIG. 5a, the board 16 closest to the discharge end of the conveyor 14 will be discharged from the conveyor as shown in FIG. 5b and the remaining boards will be restrained by the dogs 27a and 27b. When the lifters 28a and 28b are deactivated and the discharge end 26 and vertical lip 26e of the frame 26 return to the restraining position, the dogs 27a and 27b are deactivated and spiked ends thereof return to the non-restraining position. The conveyor 14 moves the boards forward until they are restrained against further movement by the vertical lip 26e. When the lifters 28a and 28b and dogs 27a and 27b are again activated, the next board will be discharged from the conveyor 14 and the remaining boards restrained. In this fashion, the restraining means operates to discharge one board at a time from the conveyor 14 and to restrain the remaining boards.

In the preferred embodiment, sense switches 30, which are suitably conventional contact switches, are mounted on the frame 11 intermediate the dogs 27a and 27b and the vertical lip 26e of the frame 26 so that each board that passes the dogs and is restrained by the lip contacts and actuates the switches. Actuation of the switches is preferably sensed by the dedicated control logic as an indication that a board is in proper discharge position on the conveyor 14. In the event that neither switch is actuated, the logic is informed that no board is in the discharge condition and that the dogs and lifters may be actuated to move another board into the discharge condition. When the logic senses that only one of the switches is actuated, it is informed that a board is improperly positioned for discharge.

The control logic may simply comprise an AND gate having inputs connected to the switches and an output connected to conventional driver circuits for activating and de-activating the dogs and lifters. The output of the AND gate is preferably synchronized with the operation of the lumber receiving means 65 by simply providing a latch such as a D-latch between the output of the AND gate and the driver circuits. The D-latch may be clocked by a signal from the proximity switch 52 associated with the indexing drive described in detail below. An XOR gate having inputs connected to the switches may be provided for detecting improper position of the board.

The loading means generally comprises an oscillating drive 36, sliding frame means 31, and a pair of identical cam follower assemblies, one of which 32 is illustrated in detail in FIGS. 3, 4, and 5a–f. The sliding frame 31 is connected to the oscillating drive 30 which drives it back and forth along a predetermined linear path parallel to the path of the conveyor 14. The cam follower assemblies 32 are connected to opposite ends of the sliding frame 31 and are driven simultaneously thereby to engage individual pieces of lumber discharged from the conveyor 14 near the opposite longitudinal ends thereof and to load the pieces of lumber into the rotatable lumber receiving means 65 described in detail below.

The oscillating drive 36 is preferably a Ferguson FD300 oscillating drive or equivalent. The oscillating drive 36 has its input shaft connected by conventional universal coupling means 36a to one end of a drive shaft 33, the opposite end of which is connected by conventional universal coupling means 60a to the output shaft of an indexing drive 60, which is described in detail below, and which drives both the rotatable lumber receiving means 65 and the oscillating drive 36.

A drive arm 34 is connected at one end to the oscillating output shaft of the oscillating drive 36 and at the other to a horizontal frame member 35 of the sliding frame means 31 by a conventional pivoting linkage member 36b. The horizontal frame member 35 is preferably constructed of a light yet durable material such as aluminum or a material having similar properties. The horizontal frame member extends perpendicularly to the path of the conveyor 14 for a distance slightly greater than the width of the conveyor 14. The horizontal frame member 35 is connected at its opposite longitudinal ends by welding, nuts and bolts, or other suitable connecting means to identical sliding frame members, a representative one 37 of which is illustrated in detail in FIG. 4. The sliding frame members 37 are in turn mounted on bearing blocks 37a and 37b which are mounted on a horizontal rod 38. The ends of the rod 38 are mounted in supports 38a and 38b which are in turn mounted on the frame 11.

The cam follower assembly 32 is mounted partially on the sliding frame member 37 and partially on the frame 11. The portion of the cam follower assembly 32 mounted on the sliding frame member 37 is mounted adjacent to the outside surface of the frame 18a, 18b of the conveyor 14. The portion of the cam follower assembly 32 mounted on the sliding frame member 37 generally comprises loading plate means 39, a pawl and latch 39b and 39c respectively, and rolling cam followers 40 and 41. The loading plate means 39, latch 39c, and cam follower 40 are mounted on a horizontal shaft 42 which is rotatably mounted in a bearing block 43 which is in turn mounted on the sliding frame member 37. The cam follower 40 is rotatably mounted to the end of the shaft 42 by a vertical extension arm 44. The loading plate means 39 has a front plate 39d which is connected to a mounting ear 39e which is in turn connected to the shaft 42. The mounting ear is pivotally connected by pivoting linkage members 45a and 45b to the sliding frame member 37. A spring 46 is connected between the linkage member 45b and the sliding frame to bias the loading plate means 39 and shaft 42 so that the front plate 39e of the loading plate means 39 is normally in a vertical position. The second cam follower 41 is rotatably mounted on a shaft 48 which in turn is connected to the pawl 39b. A spring 47 is connected between the pawl 39b and the sliding frame member 37 to bias the pawl 39b normally downward.

The portion of the cam follower assembly 32 mounted on the frame 11 comprises first and second cam follower tracks 40a and 41a. The cam follower track 40a comprises an upper track 40b and a lower track 40c, both parallel to the path of movement of the sliding frame member 37. The lower track 40c includes an inclined section 40d, the function of which is described below in detail. The cam follower 40 and cam follower track 40a are preferably positioned so that the cam follower rolls on the track 40a as the sliding frame member 37 drives the cam follower assembly back and forth. The cam follower track 41a is also parallel to the path of movement of the sliding frame member 37 and includes upper and lower sections 41b and 41c respectively, connected by an inclined section 41d. The cam follower 41 and cam follower track 41a are preferably positioned so that the cam follower 41 rolls atop the cam follower track 41a as the sliding frame member 37 drives the cam follower assembly 32 back and forth.

Referring to FIGS. 4 and 5a–f, when a board is discharged from the conveyor 14, it is supported near its opposite longitudinal ends by horizontal shelves 49 which are mounted to the side frames 18a and 18b of the conveyor 14 and which extend parallel to the conveyor 14 between the discharge point of the conveyor and a loading position of the rotatable lumber receiving means 65. A layer of Teflon or other material having a low coefficient of friction is preferably affixed by adhesive or other suitable means to the top surfaces of the shelves 49 to facilitate sliding of the boards into the lumber receiving means. As the oscillating drive 36 drives the sliding frame means 31 forward, the cam followers 40 and 41 roll forward along the respective tracks 40a and 41a. The front plates 39d of the loading plate means 39 are vertically oriented and engage the edges of the lumber 16 supported on the shelves 49 near the opposite longitudinal ends thereof. As the cam follower assemblies 32 move further forward, the front plates 39d urge the lumber 16 lengthwise and edgewise into a slot or compartment 67a of the lumber receiving means 65 which is in a loading position adjacent to and aligned with the shelves 49. As the cam follower assemblies 32 move still further forward, the cam follower 40 rolls up the inclined section 40d of the lower track 40c. As the cam follower 40 rolls up the incline, the shaft 42 rotates clockwise so that the front plate 39d of the loading plate means 39 rotates downwardly to a substantially horizontal position.

As the oscillating drive 36 reverses direction and the cam follower assemblies 32 begin moving toward the in-feed end of the conveyor 14, the cam follower 41 is on the lower potion of the cam follower track 41a. The end of the pawl 39b is biased downwardly and engages a notch 39f in the latch 39c to prevent the shaft 42 from rotating back to its original position. The cam follower 40 thus rolls along the upper track 40b until the oscillating drive 36 reaches approximately its full rearward position. At this point, the cam follower 41 is on the upper portion of the cam follower track 41a which urges the end of the pawl 39b upwardly and disengages it from the notch 39f in the latch 39c. This in turn releases the shaft 42 which rotates counterclockwise to its original starting position and rotates the cam follower 40 back onto the lower track 40c.

The foregoing operation of the loading means repeats for each board to be loaded into the lumber receiving means 65. Preferably, the oscillating drive 36 is configured with sufficient dwell time at its full rearward or "home" position to allow the lumber receiving means 65 to be rotated or indexed by the indexing drive 60 to the next position before starting forward to load the next board. Also preferably, a sensing switch 50, which may be a conventional contact switch, is mounted to the frame 11 and positioned so that it will be actuated by a board discharged from the conveyor 14 and supported in loading position on the shelves 49. The control logic described above preferably senses the actuation of the switch as an indication that a board is in loading position and that the dogs and lifters of the restraining means should not be actuated to discharge another board from the conveyor. Alternatively, the state of the switch may be sensed by the control computer means described in detail below if it is desired to have the computer control the restraining means. Once the board in the loading position is loaded into the lumber receiving means, then the unactuated switch indicates to the logic that the dogs and lifters should be actuated to discharge another board from the conveyor 14 into the loading position.

In addition, as best shown in FIG. 3, a cam 51 is preferably connected to the output shaft of the indexing drive 60 and a conventional proximity switch 52 is mounted adjacent to the cam 51. The cam 51 is preferably mounted so that it can be rotated selectively and adjusted such that its lobe is just short of actuating the switch when the lumber receiving means is fully indexed and stopped at a loading position. When the lumber receiving means is being indexed to the next position, the switch 52 is actuated to indicate that the lumber receiving means is being indexed to the next position. In this manner, the restraining and loading means operate cooperatively under control of the control logic to discharge each of the boards from the conveyor 14 sequentially into a loading position adjacent to the lumber receiving means 65.

FIGS. 2 and 3 illustrate the discharge side of the preferred classification apparatus 10. The discharge side includes a frame network indicated generally as 55. Mounted on the frame 55 is a main drive motor 56 which is preferably a conventional Reliance 15 horsepower variable speed drive motor. In the preferred embodiment the motor 56 may be suitably operated at approximately 1750 revolutions per minute which is generally suitable for use in lumber mill operations. It is understood that both lower and higher operational speeds are also acceptable. The motor 56 has an output shaft 56a which is coupled by a drive belt 57 to an input shaft 58 of a conventional reduction gear and torque limiter 59. The reduction gear 59 in turn drives the indexing drive 60. The indexing drive 60 and reduction gear 59 are preferably a Ferguson FD242 Intermittor and R400 or equivalent reduction gear having a reduction ratio of approximately 15:1. The indexing drive 60 has an output shaft (not visible) which has a toothed sprocket (not visible) mounted thereon. The indexing drive sprocket engages one end of an endless loop drive chain 61. The other end of the drive chain 61 is engaged by a toothed sprocket 62 which is mounted on a horizontal lumber receiving means drive shaft 63.

The drive shaft 63 is rotatably supported substantially horizontally by a pair of bearing blocks 64 and 64a which are mounted atop columns 64b and 64c respectively of the frame network 55 on opposite sides of the indexing drive 60. The rotatable lumber receiving means referred to above is preferably comprised of three carousel wheels 65a, 65b, and 65c, which are mounted on the drive shaft 63 perpendicular to the axis of rotation thereof, preferably at equally spaced intervals. Each of the carousel wheels 65a–c includes a mounting ring 66 for mounting on the drive shaft 63 and a plurality of fingers 67 extending radially outward therefrom to form a plurality of slots 67a for holding boards 16 length-wise and edge-wise. Each of the carousel wheels 65a–c preferably has a plurality of pieces of a mechanical isolator material 68 bolted or otherwise fastened thereto and extending partially into each of the slots 67a. The isolator material 68 preferably supports each piece of lumber 16 in each slot 67a and isolates it from mechanical vibrations in the apparatus 10 which can otherwise be transmitted into the lumber 16 and affect the results of the classification analysis. In the preferred embodiment, one-quarter inch thick, grade 500A virgin Teflon is utilized for the isolator material 68. Alternatively, other isolator materials such as rubber may be used, but are not preferred since such materials tend to compress under force and to oppose the sliding motion of the lumber 16 into the grading position as described in detail below.

In the preferred embodiment, each of the carousel wheels 65a–c is provided with eight slots 67a. The carousel wheels 65a–c are mounted on the drive shaft 63 so that corresponding slots 67a of each wheel are aligned to support a piece of lumber 16 edge-wise at selected points along its length. The mounting rings 66 of the carousel wheels 65a–c are preferably slideable horizontally on the drive shaft 63 so that different lengths of lumber can be accommodated. The rings 66 are preferably provided with locking means so that they can be locked into a selected position on the shaft 63. For example, the rings 66 may be drilled and tapped so that set screws can be used to hold them in place on the shaft 63. Alternatively, locking rings or other conventional locking means can be used.

The preferred indexing drive 60 and reduction gear 59 are configured to drive the drive shaft 63 with eight stops or positions per revolution of the shaft corresponding to the eight slots or positions of the carousel wheels 65a–c at a rate of approximately 100 positions per minute. The indexing sprocket and the sprocket 62 are preferably configured in a manner well known in the art to convert the output angle of each increment of the drive 60 to a 45 degree rotation of the shaft 63.

The top slot position of the carousel wheels 65a–c is designated as the grading position. In this position, a piece of lumber 16 is supported in the slots 67a substantially vertically and edge-wise for grading by the apparatus 10. As the carousel wheels 65a–c index after a piece of lumber 16 has been graded, the lumber may be manually removed from the slots 67a on the discharge side after being automatically marked, stamped, or otherwise identified with a classification indicia corresponding to selected calculated characteristics of the lumber. Alternatively, the lumber may be manually removed and then manually identified with a classification indicia corresponding to classification information displayed on an operator terminal or other display media. Also alternatively, the lumber may be discharged directly onto a conveyor (not shown) and transported thereby to a remote location for further processing such as sorting. At the same time a new piece of lumber to be classified is loaded into the carousel wheels 65a-c on the in-feed side of the apparatus in the manner described above.

An impactor means 75 is mounted in a housing 69 adjacent to a first longitudinal end of the piece of lumber 16 when in the grading position and a detector means 165 is mounted adjacent to a second opposite longitudinal end of the lumber 16 when in the grading position. The housing 69 is mounted by conventional means to a horizontal beam 70 which extends over the carousel wheels 65a-c. A surface 110 of a transmitter head, which is described in detail below, extends from the housing 69.

The detector means 165 is mounted for horizontal movement on a horizontal rod 71. The rod 71 is supported by a support member 72 which is in turn mounted on tracks 72a or other equivalent structure for horizontal movement on the beam 70. The position of the support member 72 on the beam 70 may thus be adjusted to accommodate different lengths of lumber 16. Preferably, the support member 72 is provided with locking means of some type to prevent movement from the selected position on the beam 70.

Also mounted to the support member 72 is a pneumatic cylinder 73 (sometimes referred to herein as an "air" cylinder). The pneumatic cylinder 73 is connected to the back of the detector means 165. The control computer 225, which has been referred to above and which is described in detail below, selectively energizes and de-energizes the pneumatic cylinder 73 to extend and retract to move the detector means 165 into and out of contact with the piece of lumber 16 in the grading position. When energized, the pneumatic cylinder 73 extends and forces the detector means 165 to contact a first longitudinal end of the lumber 16 and to urge the lumber 16 to slide in the slots 67a of the carousel wheels 65a-c so that the second opposite longitudinal end of the lumber 16 comes into contact with the surface 110 of the impactor means 75. The control computer then generates a control signal to energize the impactor means 75 to impact the second longitudinal end of the lumber 16 and to detect and analyze the resulting signal generated by the detector means 165 in response to the compression force induced at the first opposite longitudinal end of the lumber 16 to determine preselected physical parameters such as MOE and MOR for the lumber and assign a corresponding grade classification thereto as described below. After a piece of lumber is impacted, the computer 225 de-energizes the pneumatic cylinder 73 to retract the detector means 165. Preferably, the support member 72 is positioned so that there is adequate clearance between the end of the board 16 and the detector means 165 which the pneumatic cylinder is retracted to allow the carousel wheels 65a-c to index the next piece of lumber 16 into grading position without interference from the detector means 165. In the preferred embodiment, the pneumatic cylinder is driven by approximately 90 psi of air pressure in order to provide secure clamping of the board 16 during the grading process.

Preferably, a sense switch (not visible), which is suitably a conventional contact switch, is mounted adjacent to the grading position of the carousel wheels 65a-c and is actuated each time a piece of lumber 16 is indexed into the grading position. Actuation of the switch is preferably sensed by the control computer 225 as an indication that a board is in position and ready for the grading process to begin.

In addition, a conventional pressure-actuated switch 74 is preferably connected to the pneumatic cylinder 73 to identify to the computer 225 whether sufficient air pressure is present to clamp a board 16 to perform the grading process.

A detailed description of the operation of the preferred classification apparatus is set forth below. Generally, however, boards 16 are loaded onto the conveyor 14. The conveyor 14 is energized by a signal from the computer and transports the boards 16 into the grading portion of the apparatus. The carousel wheels 65a-c index position by position and for each index cycle, a board is loaded into a slot 67a in the wheels at the loading position as described above. As each board 16 reaches the grading position at the top of the carousel wheels 65a-c, the pneumatic cylinder 73 clamps the board 16 into grading position between the impactor means 75 and detector means 165 at opposite longitudinal ends thereof. The impactor means 75 impacts one longitudinal end and the detector means 165 detects the compression force induced thereby in the opposite longitudinal end thereof. The detector means generates an electrical signal corresponding to the detected compression force. The signal is analyzed in a manner described in detail below and predetermined physical parameters (MOE and MOR in the preferred embodiment) are calculated for the board 16. The values of these parameters are used to determine a grade classification for the board. The pneumatic cylinder 73 unclamps the board and retracts detector means 165. The carousel wheels index to move the graded board out of grading position and a new board into grading position. At the same time a new board is loaded into the slots 67a of the carousel wheels 65a-c in the loading position. The control computer 225 activates a mechanical stamp, paint cylinder, or other marking means to apply an appropriate grade classification indicia corresponding to the calculated parameters to the graded board. Alternatively, an operator marks the graded board with the determined classification indicia and the board is unloaded from the carousel wheels 65a-c. The cycle is repeated for each board 16 to be classified.

FIG. 6 illustrates the details of the preferred impactor means 75. As mentioned above, the impactor means 75 is mounted in the housing 69. The housing 69 includes front and back walls 76 and 78, a bottom wall 80, and top and side walls (not shown). The impactor means 75 generally comprises a hammer solenoid 82, a transmitter head 84, and an armature thrust control spring 86.

The solenoid 82 is mounted on the bottom wall 80 of the housing 69 by nuts and bolts such as representative nuts and bolt 88, 88a, 90, and 90a, or other conventional means. Preferably, slots (not shown) are machined or otherwise provided in the bottom wall 80 to accommodate the bolts 88 and 90 as well as to provide a range of selectable positions for the solenoid 82. The solenoid 82 includes an armature 92 which is mounted within the aperture of the solenoid coil (not shown) in a manner well known to those skilled in the art. The armature 92 has mounted thereon an armature return stop 94. The armature return stop 94 is a cylindrical metal piece which has a diameter slightly greater than the diameter of the armature 92 and slightly greater than the solenoid aperture (not shown) through which the armature 92 protrudes. The armature return stop 94 may be mounted on the armature 92 by drilling and tapping the armature return stop 94 and armature 92 and inserting a set screw 96 or other threaded fastening means. The placement of the armature return stop 94 on the armature 92 determines the extent to which the body of the armature 92 will be seated within the aperture of the solenoid coil when the solenoid 82 is de-energized and the range of travel of the armature 92 when the solenoid 82 is energized. A hammer 98 is also mounted on the armature 92 at the end thereof similarly to the armature return stop 94 by a set screw 100. The hammer 98 has a beveled end 101 with a solid flat face 102 and a hollow, cylindrical interior having a diameter sufficient to fit in secure, abutting contact with the armature 92 when placed over the end thereof.

The transmitter head 84 is preferably a machined piece of solid steel having a cylindrical body 104 and a circular flange 106 formed thereabout perpendicularly to the central axis of the body 104. One end of the cylindrical body 104 is beveled down to a flat impact surface 108. The opposite end of the cylindrical body 104 has machined therein a plurality of points or teeth 110. A cylindrical opening 112 having a diameter slightly larger than that of the cylindrical body 104 is machined in the front wall 76 of the housing to receive the cylindrical body 104. A cylindrical countersunk cavity 114 is machined into the front wall 76 concentrically with the cylindrical opening 112. The diameter of the cavity 114 is preferably slightly larger than the diameter of the flange 106 of the transmitter head 84. The depth of the countersunk cavity 114 and the position of the flange 106 are preferably selected so that a portion of the cylindrical body 104 having the points 110 extends beyond the outside surface of the front wall 76 of the housing 69. The cylindrical opening 112 is machined so that when the transmitter head 84 is mounted therein the cylindrical body 104 and the flat, circular impact surface are concentric with the face 102 of the hammer 98. A cylindrical steel retainer plate or washer 116 which has a diameter slightly larger than the diameter of the countersunk cavity 114 is mounted to the front wall 76 by screws 115 and 117 and retains the transmitter head 84 in its mounting position in the front wall 76.

It is critical that the transmitter head 84 be isolated from the front wall 76 so that substantially all of the impact energy applied to it by the hammer 98 when the solenoid 82 is energized is transmitted to the material to be classified or graded and not transmitted into the front wall 76. Likewise, it is critical to isolate the transmitter head 84 from the front wall 76 so that vibrations induced in the front wall 76 during operation of the classification apparatus are not transmitted by the transmitter head 84 to the lumber to be classified or graded.

Accordingly, a plurality of isolation rings 118 preferably in the form of rubber "O" rings are mounted around the section of the cylindrical body 104 which is mounted within the cylindrical opening 112. In addition, a compression washer 120 and an isolation washer 122 having diameters approximately equal to the diameter of the circular flange 106 are mounted on opposite sides thereof with the compression washer 120 being mounted between the flange 106 and the front wall 76 and the isolation washer 122 being mounted between the flange 106 and the retainer plate 116. The compression washer 120 is preferably a rubber washer of the type commonly used as gasket material. The isolation washer 122 is preferably grade 500A virgin Teflon. As described below, the compression washer 120 not only provides isolation between the transmitter head 84 and the front wall 76, but also allows a slight amount of movement of the transmitter head 84 when impacted by the hammer 98 to minimize the plastic zone between the lumber to be classified and the transmitter plate 84.

To further minimize the plastic zone between the transmitter head 84 and the lumber to be classified, it is preferred that the points 110, which are provided for engaging the lumber, be approximately 3/16 inch deep and be filed flat. This arrangement tends to maximize the surface contact between the end of the lumber, which in practice can be quite uneven and ragged, and the transmitter head 84. At the same time, the use of flat points prevents deformation of the lumber and consequent disruption of the compression force at impact. Other configurations, such as a flat face, may be found suitable for use with other types of materials having smoother, less ragged surfaces. In addition, to maximize the transfer of impact energy from the hammer 98 to the lumber, it is preferred that the transmitter head 84 be constructed of steel having at least 1044 gauge hardness and having the grain running parallel to the direction of impact.

An impact detector is preferably placed in contact with the transmitter head 84 to sense the impact of the impactor means 75 against the transmitter head 84. In the preferred embodiment, an impact accelerometer 148 is mounted to the transmitter head 84 by drilling and tapping a hole approximately ⅜" in depth in the head 84 and mounting the accelerometer 148 accordingly. The output of the accelerometer 148 is connected to an input of the data acquisition circuitry described in detail below and generates a data acquisition signal on impact to notify the data acquisition electronics that impact, i.e., the condition of interest, has occurred. The accelerometer 148 is suitably any conventional accelerometer. Alternatively, since there is a certain potential associated with the armature 92 and since the preferred transmitter head 84 is constructed of an electrically conductive material, the transmitter head 84 can be electrically connected to an input port of the computer or data acquisition electronics and contact between the armature 92 and the transmitter head 84 itself used to signal impact. Other impact sensing means known in the art, such as contact switches, may also be used.

In order to maximize the accuracy and repeat ability of the results, it is desirable for the hammer 98 to impact the transmitter head 84 with the same force each time the hammer solenoid 82 is energized. It is also desirable for the force to be within certain limits to produce a signal having characteristics suitable for analysis. These objects are accomplished in the preferred embodiment by adjusting the travel of the armature 92 prior to the face 102 of the hammer 98 striking the face 108 of the transmitter head 84 and by controlling the thrust of the armature at impact.

Optimally, the travel of the armature 92 is adjusted such that each time the solenoid 82 is energized the face 102 of the hammer 98 actually just "taps" the impact surface 108 of the transmitter head 84. Accordingly, it is desirable to adjust the position and travel of the armature 92 prior to impact. The position and travel of the armature 92 are controlled by the positioning of the armature return stop 94 on the armature 92 and by the positioning of the solenoid 82 on the bottom wall 80 of the housing 69. The position of the solenoid 82 on the bottom wall 80 is preferably maintained by a front 124 and a rear 126 spacer block which fit in abutting contact between the front of the solenoid 82 and the front wall 76, and the rear of the solenoid 82 and the back wall 78 respectively. Fine adjustment of the position of the solenoid 82 may be provided by front 125 and rear 127 spacer shims between the front 124 and rear 126 spacer blocks and the front and rear of the solenoid 82 respectively. Preferably, the armature return stop 94 and the position of the solenoid 82 on the bottom wall 80 are cooperatively adjusted so that at least a portion of the armature 92 remains within the aperture of the coil of the solenoid 82 to reduce heating of the coil and optimize response when the solenoid is energized.

The armature thrust control spring 86 precisely controls the contact time of the impact force applied by the hammer 98 to the transmitter head 84 each time the solenoid 82 is energized. The armature thrust control spring 86 is suitably a conventional steel coil-type spring which is capable of providing at least 20 pounds of tension. A Barnes 6¾" spring number E0360-034-2500 spring has been found suitable. One end of the spring 86 is connected to a mounting fixture 130 which forms a portion of the armature 92 by a suitable connecting link 132. The other end of the spring 86 extends through an opening 134 machined in the back wall 78 of the housing 69 into a hollow, elongated spring housing 136 and connects to an end of a tension rod 138. The housing 136 has a diameter slightly smaller than the diameter of the opening 134. The housing 136 is fitted within the opening 134 and is held in place by a pair of lock nuts 140. A cylindrical cap 142 having a central opening (not shown) caps the opposite end of the housing 136. The tension rod 138 extends through the aperture in the cap 142 and through an adjusting nut 144. The tension rod 138 is provided with a threaded section 146 which mates with corresponding threads of the adjusting nut 144. By rotating the adjusting nut 144, the tension exerted by the spring 86 on the armature 92 in a direction opposite to the direction of impact can be precisely adjusted.

In the preferred embodiment, the solenoid 82 is driven by a high voltage AC power source in response to control signals from the control computer 225 as described in detail below. In this embodiment, it has been found beneficial to adjust the spring tension so that the armature is held against movement in the direction of impact until approximately 5° prior to top dead center of the AC waveform. At approximately 5° prior to top dead center, the solenoid has built up a sufficient electromagnetic field to overcome the spring tension to thrust the armature 92 in the direction of impact and to cause the hammer 98 to impact the transmitter head 84 at approximately top dead center of the AC waveform. At this point, the armature has maximum thrust and applies maximum impact force to the transmitter head 84. In addition, by delaying the armature 92 movement until near the top of the AC waveform, rapid acceleration of the armature 92 and hence the hammer 98 is obtained. The spring 86 thus establishes a sort of reference for the impactor means 75 and precisely controls the timing of the impact force applied to the transmitter head 84 relative to this reference. In addition, the spring 86 rapidly retracts the hammer 98 from the transmitter head 84 when the hammer solenoid 82 is de-energized, thereby minimizing the transmission of any "chatter" between the hammer 98 and transmitter head 84 into the board 16.

In the preferred embodiment, the response and acceleration of the armature 92 and hence the impact force of the hammer 98 are further maximized by driving the solenoid 82 in a current in-rush mode at approximately twice its normal rating. Thus, a solenoid rated at 115 V is preferably driven at approximately 230 V and a solenoid rated at 230 V is preferably driven at approximately 460 volts. At this voltage, it is desirable to drive the solenoid 82 for only one to one and a half cycles of the AC waveform. Thus, the hammer solenoid 82 used in the preferred embodiment must be able to withstand high in-rush currents at double its rated voltage capacity for short durations, and be able to develop a sufficient electromagnetic field in one to one and a half cycles of the AC waveform to overcome the tension of the spring 86 and impact the transmitter plate 84. In the preferred embodiment, a Model 5600 push-pull type industrial solenoid Model No. 42-05604 rated at 230 volts available from Stearns, Milwaukee, Wis., has been found suitable for use at a preferred drive voltage of 480 VAC.

Using the preferred Stearns solenoid, in the preferred embodiment highly accurate and repeatable results have been obtained by adjusting the spring 86 using a strain gauge to provide 20 to 25 pounds of tension on the armature 92, and adjusting the positions of the solenoid 82 and armature return stop 94 to provide approximately ⅜" of travel of the hammer 98 prior to impact with the transmitter head 84.

FIGS. 7a through 7c illustrate the details of the preferred detector means 165 of the invention. The detector means 165 includes an elongated cylindrical pick-up rod 170 which is mounted vertically to a front plate 168 in such a manner that approximately one-third of the circumference of the rod 170 extends outwardly beyond the front surface of the front plate 168. The manner of mounting the pickup rod 170 to the front plate 168 is described in greater detail below. A clevis ear 180 is connected to the front plate 168 by a plurality of threaded bolts 176. Countersunk wells 174 are machined or otherwise provided in the front surface of the front plate 168 so that the heads of the bolts 176 are recessed in the front plate 168. Isolation washers 178, preferably of Teflon, isolate the heads of the bolts 176 from the surface of the front plate 168. Holes are drilled through the front plate 168 and into the clevis ear 180 to accommodate the bolts 176. The holes drilled in the clevis ear 180 are tapped to receive the threaded sections of the bolts 176. An isolation shim 184 is preferably positioned between the clevis ear 180 and the front plate 168 to isolate the two components.

The front plate 168 is connected by an angle bracket 186 to a horizontal mounting block 188. The front plate 168 is connected to a vertical section of the angle bracket 186 by a plurality of threaded bolts 192 and corresponding nuts 194. Countersunk wells 190 are machined or otherwise provided in the front plate 168 so that the heads of the bolts 192 are recessed below the front surface of the front plate 168. The horizontal mounting block 188 is connected to the horizontal section of the angle bracket 186 by a plurality of threaded bolts 195 and corresponding nuts 197. Countersunk wells 199 are machined or otherwise provided in the top surface of the mounting block 188 so that the heads of the bolts 195 are recessed below the top surface.

A bearing support plate 196 is mounted horizontally flush with the top surface of the mounting block 188 in a damped arrangement by a plurality of threaded bolts 202 and corresponding nuts 204. Countersunk wells 208 are provided in the bottom surface of the mounting block 188 so that the heads of the bolts 202 are recessed below the surface of the mounting block 188. The length of the bolts 202 is preferably selected to provide sufficient excess vertical space for the mounting of a cylindrical spring 206 onto the bolt 202 between the top surface of the bearing support plate 196 and the bolt 204. The springs 206 provide damping so that when the detector means 165 moves on the rod 62 any vibrations due to such movement are damped and prevented from being transmitted to the pickup rod 170. A bearing block 198 having a cylindrical aperture 200 is mounted with the aperture oriented horizontally to the bearing support plate 196 by a plurality of threaded bolts 199 and corresponding nuts 201. Countersunk wells 203 are provided in the top surface of the mounting block 188 for each of the heads of the threaded nuts 199 so that the bearing support plate 196 fits flush with the top surface of the mounting block 188. The cylindrical rod 71, illustrated in FIG. 2, runs through the aperture 200 and supports the detector means 165 for horizontal movement thereon as described above.

As best shown in FIGS. 7b and 7c, a key-shaped vertical, slotted opening 172 is machined or otherwise provided in the front plate 168 to receive the cylindrical pickup rod 170. A hole is drilled through the back of the front plate 168 at the mid point of the vertical dimension of the slot 172 to receive a threaded stud 210. A one-quarter inch layer of silicone gel 214, such as G.E. Clear Silicone Gel, No. 361, is initially inserted into the bottom of the slot 172 and allowed to cure. The cylindrical pickup rod 170 is provided with a threaded hole which is aligned with the hole drilled in the back of the front plate 168. After the initial layer of the silicone gel 214 has cured, the pickup rod 170 is mounted atop the initial layer and bolted into place by the threaded bolt 210. Then, the remainder of the slot is filled with silicone gel 214 such that the area between the bolt 210 and the walls of the front plate 168 and the area between the pickup rod 170 and the walls of the front plate 168 are completely filled with gel 214. The gel 214 is inserted until flush with the front surface of the front plate 168 and is then allowed to cure. A transducer means in the form of a conventional accelerometer 212 is then attached by conventional means to the head of the stud 210. The accelerometer is suitably a Columbia 3029 or equivalent accelerometer. The output of the accelerometer 212 is electrically connected to the input of the data acquisition circuitry 230 which is described in detail below.

The clevis ear 180 of the detector means 165 is provided with a flat contact surface 182 opposite the back side of the front plate 168. The flat contact surface 182 is adapted to be attached to the pneumatic cylinder 73 as illustrated in FIG. 2 and described above so that when the cylinder 73 is energized, the cylinder urges the detector means 165 horizontally along the cylindrical 71 rod and urges the front surface of the pickup rod 170 into contact with the end of the piece of lumber 16 as described above.

FIG. 8 is a block diagram illustrating generally the electronic control and processing components of the presently preferred embodiment of the automated material classification apparatus of the invention. The heart of the electronics is a control computer 225, which is described in detail below. A conventional operator terminal 228, such as a so-called dumb terminal, is connected to an I/O port of the computer 225 by conventional cable and interface means. Also connected to I/O ports of the control computer 225 in a similar known fashion are inputs and outputs of data acquisition circuitry 230. The data acquisition circuitry 230 comprises signal conditioning circuitry 232, an analog to digital (A/D) converter 234, a memory address counter 236, timing circuitry 238, and data memory 240. The input of the signal conditioning circuitry 232 is connected to the output of the data accelerometer 212 and the output of the signal conditioning circuitry 232 is connected to an analog data input of the A/D converter 234. The A/D converter 234 converts the conditioned analog signal to digital words and outputs the digital words directly to the data memory 240. The timing circuitry 238 has outputs connected to the data memory 240 and to the memory address counter 236. The timing circuitry 238 controls the operation of the memory address counter 236 and data memory 240 to read and store the digital words generated by the A/D converter at appropriate times and to output the stored digital words to the control computer 225 at appropriate times as described in detail below. The timing circuitry 238 has an input connected to an output of trigger conditioning circuitry 242 which in turn has an input connected to an output of the impact detector 148 described above. The data acquisition electronics 230 and the trigger conditioning circuit 242 are both described in detail below.

The control computer 225 also has a plurality of output ports connected to inputs of a plurality of relay drivers 246, which are suitably 74LS244 tri-state line drivers or equivalents. The outputs of the relay drivers 246 are connected to inputs of conventional control relays 248, which are suitably Microelectronic model 240PS10 solid-state, optically-isolated relays or equivalents. Each of the control relays 248 is connected with one control terminal being connected to the output of the corresponding relay driver 246 and the other control terminal being grounded. The first AC terminal of each control relay 248, with the exception of the control relays associated with the hammer solenoid 82, is connected to the AC output of a 110 volt AC power source. The second AC terminal of each relay 248, with the exception of the relays associated with the hammer solenoid 82, is connected to one end of the coil of a solenoid 250, the other end of which is connected to the neutral side of the 110 volt AC power source. The control computer 225 generates control signals for the relay drivers 246 to selectively energize and de-energize control relays 248 to selectively energize and de-energize solenoids 250 to thereby selectively control the operation of the components of the apparatus 10. The solenoids 250 in turn operate the impactor means 75, as described above, identification means 256, which may be a stamp, paint sprayer, or other marking means to apply a classification indicia to classified lumber, the conveyor 14, and the air cylinder 73 to clamp a board to be classified between the impactor means 75 and detector means 165 as described above.

A plurality of switch conditioning circuits 254 have outputs connected to input ports of the control computer 225. The inputs of the switch conditioning circuits 254 may be connected to outputs of a correspondig plurality of sense switches 252. As described above, the sense switches 252 preferably include contact switches mounted adjacent to the discharge position of the conveyor 14, the load position, and the grading position, a proximity switch 52 mounted adjacent to the cam of the indexing drive 60, and a pressure switch 74 connected to the pneumatic cylinder 73. In the preferred embodiment, the pressure switch 74, grading position switch and proximity switch are connected to the computer 225 while the remaining switches are connected to separate control logic as described above. Alternatively, all of the sense switches could be connected to the computer 225. The switch conditioning circuitry 254 suitably comprises 74LS279 R-S latches or equivalents which are used to latch and debounce the signals generated by the sense switches 252.

FIG. 9 is a schematic diagram which illustrates the details of the control relay arrangement used with the hammer solenoid 82 of the impactor means 75. Two solid state relays 248a and 248b of the preferred type are employed to control the energization of the hammer solenoid 82 to operate the hammer solenoid 82 in a high current in-rush mode, as described above. Both relays 248a and 248b have their positive control terminals connected to an output of a relay driver 246. The negative control terminals of both relays 248a and 248b are connected to ground. The first AC terminal of relay 248a is connected to one side of a 480 volt AC power source. The first AC terminal of the relay 248b is connected to the other side of the 480 volt AC power source. The second AC terminals of the relays 248a and 248b are connected to opposite ends of the coil of the hammer solenoid 82. When a board is in grading position, the control computer 225 outputs a control signal to the relay driver 246 corresponding to the impactor means 75. The relay driver 246 in turn energizes the control relays 248a and 248b which connects the coil of the hammer solenoid 82 directly between the 480 volt and ground terminals of the 480 volt AC power source. As described above, once the solenoid 82 is energized, it develops a sufficient electromagnetic field to thrust the armature forward to impact the transmitter head 84 of the impactor means 75 within one to one and one-half cycles of the AC waveform. The solenoid 82 remains energized until the control computer 225 removes the control signal which causes the relay driver 246 to de-energize the control relays 248a and 248b. Operation of the control relays 248 corresponding to the pneumatic cylinder 73, identification means 256, and conveyor 14 is similar, except that a single relay is used to energize the solenoids for each of these components.

FIG. 10 is a schematic and block diagram which illustrates the details of the data acquisition circuitry 230. The signal conditioning circuitry 232 is preferably conventional, impedance matching and scaling circuitry 294 which is well known to those skilled in the art. The impedance matching and scaling circuitry 294 matches the output impedance of the data accelerometer 212 and the input impedance of the analog data input terminal of the A/D converter 234. The impedance matching and scaling circuitry 294 also scales the output signal of the data accelerometer 212 so that the signal is restricted to a range of $+/-10$ volts which is the maximum signal voltage range of the preferred A/D converter, identified below.

The A/D converter 234 is preferably a high speed A/D converter capable of operating at at least 500 KHz, and having a high degree of digital resolution. An A/D converter which has been found to possess the preferred characteristics is the Analog Devices HAS-1204 A/D converter. This A/D converter has 12-bit resolution and operates at word output rates of 500 KHz. Accordingly, this A/D converter and equivalents are preferred for use. The twelve data output terminals of the A/D converter 234 are connected to corresponding data input terminals of the data memory 240. The data memory 240 comprises a 16-bit RAM 260, which is suitably comprised of two $8K \times 8$ Hitachi HM6264LP-10 high speed static CMOS RAMs configured as an $8K \times 16$ RAM memory. The data memory 240 also comprises a pair of tri-state input buffers 266 and 268, and a pair of tri-state output buffers 262 and 264. Each of the buffers is suitably a 74LS541 or equivalent 8-bit buffer. The eight low order digital output bits D0–D7 of the A/D converter 234 are connected to data inputs of the input buffer 268 and the four high order digital output bits D8–D11 are connected to data inputs of the input buffer 266. The data output terminals of the input buffers 266 and 268 are in turn connected to corresponding data input terminals D0-D15 of the RAM 260. The data terminals D0–D15 of the RAM 260 are also connected to corresponding data input terminals of the output buffers 262 and 264 with the eight low order bits D0–D7 being connected to data inputs of the output buffer 264 and the eight high order bits D8–D15 being connected to data outputs of the output buffer 262.

The memory address counter 236 is preferably a 16-bit counter comprised of two eight bit 74LS393 binary counters or equivalents. The output terminals of the counter 236 are connected to the corresponding address lines of the RAM 260 in a fashion well known to those skilled in the art. The address counter 236 includes clear CLR and clock CLK terminals which are connected to outputs of the timing circuitry 238 as described in detail below. The counter 236 output terminal representing the value $2^{13}$ is connected to an input of the timing circuitry 238 also as described in detail below.

The timing circuitry 238 comprises D-latches 270, 272, 274, 276 and 278, J-K flip-flop 280, NAND gate 275, OR gates 282 and 284, and AND gates 286 and 288. In addition, the timing circuitry 238 includes a divide-by-two circuit 290 and a negative-edge-triggered 90nS one-shot. The timing circuitry 238 receives as inputs counter clear CNTRCLR, sample period enable ENAB, and inverted data read /READ signals from the control computer 225. The timing circuitry 238 also receives a data acquisition or trigger signal TRIGGER from the trigger conditioning circuitry 242 and the 2 MHz clock signal E of the control computer 225. The timing circuitry 238 generates output signals which control the read and write state of the RAM 260, enable the input and output buffers 262, 264, 266, and 268, and trigger the A/D converter 234. The timing circuitry 238 also generates a sample period enable acknowledgement signal SFF and a sample period completed signal END which are communicated to input ports of the control computer 225.

In operation, the data acquisition circuitry 230 receives the analog signal generated by the data accelerometer 212 when a piece of lumber to be classified is impacted by the impactor means 75, samples the analog signal and converts it to 12-bit digital words, stores the digital words in the RAM 260, and subsequently reads the digital data words out of the RAM 260 and sends them to the control computer 225 for analysis. Depending upon the position of a jumper 277 in the timing circuitry 238, sampling can be initiated directly by the computer 225 by sending a high ENAB signal, or by a high TRIGGER signal from the trigger conditioning circuit 242 after a high ENAB signal enables the start of a sample period. The occurrence of the ENAB or TRIGGER signal (depending on the jumper 277 setting) sets the output of the D-latch 276 which generates a low enable sample period acknowledgement signal SFF which identifies to the control computer 225 that sampling has been initiated.

The timing circuitry 238 generates a 500 KHz sample clock signal from the 2 MHZ computer clock signal using the D-latch 272 and the divide-by-two circuit 290. The 500 KHz sample clock signal appears at the output of the divide-by-two circuit 290 and is used to drive the 90 nS pulse generator circuit 292. The pulse generator circuit 292 generates 90nS pulses coincident with the negative edge of the 500 KHz sample clock signal at its output. The 90nS pulses are conducted to the ENCODE terminal of the A/D converter 234 and cause the A/D converter 234 to sample the scaled analog signal appearing at the output of the impedance matching and scaling circuit 294.

The positive going edge of the 500 KHz sample clock signal clocks the address counter 236 to increment the RAM 260 address. On the first positive going edge of the 500 KHz clock signal following the initiation of a sample period, the outputs of the D-latch 278 enable the input buffers 266 and 268 and the RAM 260 to receive and store 16-bit digital words. Thereafter, each time the A/D converter 234 generates a low DATA READY signal, indicating that a 12-bit digital sample word is ready, the buffers 266 and 268 input the 12-bit word and output a 16-bit digital sample word, the low order 12-bits of which are the output of the A/D converter 234, to the RAM 260 which stored it. The data acquisition circuitry 230 continues to generate and store 16-bit digital sample words characterizing the analog data accelerometer signal in sequential locations of the RAM 260 without intervention of the control computer 225 until the entire RAM 260 is filled.

On the next positive going edge of the sample clock signal after the RAM 260 is filled, the address counter 236 output line corresponding to the value $2^{13}$ goes high. This address line is decoded by D-latch 274 and OR gate 282 which clear the address counter 236, generate a low sample period end signal END to signify to the control computer 225 that the sample period has been completed, and clear the output of the D-latch 276 to cause the enable sample period acknowledge signal SFF to go high.

When the control computer is ready to read the digital sample data from the RAM 260, it first generates a low counter clear signal CNTR CLR to reset the output of the address counter 236. The computer next generates a low read signal /READ to enable the output buffers 262 and 264 to read the 16-bit digital sample words from the RAM 260 and to send them to the control computer 225. So long as the END signal remains low, a high signal is present at the Q output of the D-latch 278, which holds the input buffers 266 and 268 disabled so that no data can be written into the RAM 260. As described in detail below, the control computer 225 in the preferred embodiment is an 8-bit computer. The computer 225 therefore reads the 16-bit digital sample words from the RAM 260 8-bits at a time. To read the data, the computer 225 generates a string of READ pulses. The negative edge of each READ pulse clocks the J-K flip-flop 280 to alternately enable the output buffers 262 and 264. Odd /READ pulses enable the RAM 260 and the output buffer 262 to output the eight high order bits D8-D15 of a 16-bit word to the computer 225. Even /READ pulses enable the RAM 260 and output buffer 264 to output the eight low order bits D0-D7 of a word to the control computer 225. The address counter 236 is clocked on the negative-going edge of every other /READ pulse to increment the RAM address after every pair of 8-bit bytes has been read.

In the preferred embodiment, it has been found that approximately 575 16-bit sample words correspond to approximately one cycle of the analog signal. Accordingly, it is adequate to read approximately 575 16-bit sample words from the RAM 260 into the computer 225 for analysis. It is preferable to analyze a number of samples corresponding to at least one cycle in order to accurately calculate the preferred MOE and MOR parameters for each board. It is apparent, however, that additional sample words are stored in RAM 260 and are available for analysis as needed or desired. It is also understood that more or fewer sample words may be read into the computer 225 for analysis depending on the requirements for the material to be classified.

Following reading of the desired number of sample words into the computer 225, on the next occurrence of an ENAB or a TRIGGER signal (depending on the setting of jumper 277), the address counter 236 is again cleared and another sample period is initiated, as described above. Thus, each time the control computer 225 issues a command to impact a piece of lumber 16 and each time an impact is detected, a new sample period may be automatically initiated by the data acquisition circuitry 230 without intervention of the computer 225 and synchronized with the occurrence of the condition of interest, i.e., generation of the compression force in the lumber being graded. Thereafter, the data acquisition circuitry 230 accumulates a plurality of digital sample words defining the data accelerometer 212 analog output signal, and when the data acquisition circuitry memory is completely filled, the data acquisition circuitry 230 signals the computer 225 to read the data. The data acquisition circuitry 230, by operating without intervention of the control computer 225, frees the control computer 225 for other tasks, such as analyzing previous digital sample words stored in the computer memory, or attending to certain control functions.

FIG. 11 is a block diagram which illustrates additional details of the trigger conditioning circuit 242 which is shown generally in FIG. 8. The trigger conditioning circuit 242 comprises a linear amplifier 300, which may be a suitably biased operational amplifier, a full wave rectifier 302, which is suitably a conventional diode bridge, a conventional TTL clamp circuit 304, and a conventional one-shot 306. The linear amplifier 300 amplifies the signal from the impact accelerometer 148 with a fixed gain. The full wave rectifier 302 rectifies the amplified signal and the TTL clamp circuit 304 clamps the signal to a TTL logic level. The signal output by the TTL clamp circuit 304 triggers the one-shot 306 which in turn outputs a digital TRIGGER signal. Preferably, the TRIGGER signal has duration less than the time required to completely fill the RAM 260 of the data acquisition circuitry 230 with digital sample words as described above. In the preferred embodiment, at the preferred sample rate of approximately 500 KHz it takes approximately 16 milliseconds to completely fill the 8K RAM 260.

Figure 12:
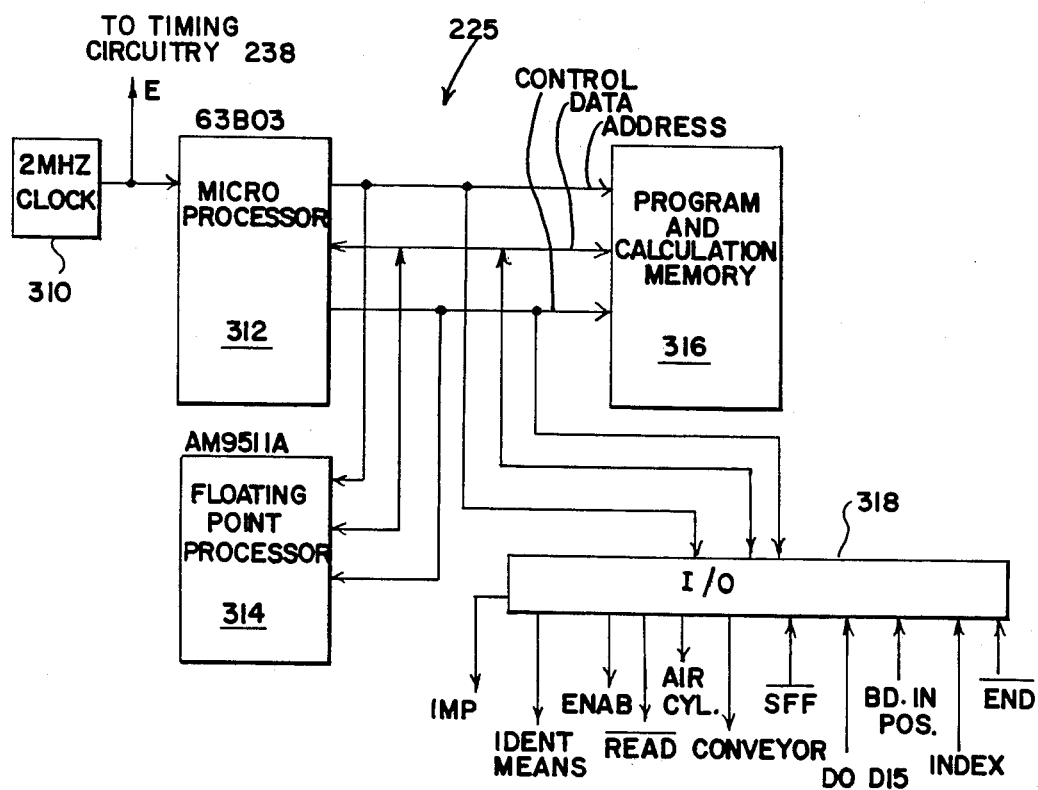
FIG. 12 is a block diagram illustrating the details of the control computer shown generally in FIG. 8.

FIG. 12 is a block diagram which illustrates the details of the control computer 225. The preferred control computer 225 comprises a conventional 8-bit microprocessor 312, a floating point processor 314, program and calculation memory 316, an I/O interface 318, and a 2 MHz clock 310 which drives the microprocessor 312 and which supplies clock signals E to the timing circuitry 238 of the data acquisition circuitry 230. The microprocessor 312 is suitably a conventional 63B03 microprocessor or equivalent. The microprocessor 312 is connected to the program and calculation memory 316 by control, data, and address lines in a manner well known to those skilled in the art. In addition, the microprocessor 312 is connected to a conventional floating point processor 314, which is suitably an AM9511A or equivalent floating point processor, also by control, data, and address lines as is well known to those skilled in the art. The floating point processor 314 is able to quickly perform arithmetic operations involving decimal point numbers, and is accordingly a preferred component of the control computer 225, which must be able to quickly and accurately compute the preferred MOE and MOR values from a selected predetermined formula or formulas, which typically contain a plurality of decimal point coefficients. In addition, the parameter values derived from the digital sample words in the manner described below are also typically decimal point values.

The I/O interface 318 is likewise connected in a well known fashion to the microprocessor 312 via the address, data, and control lines. The I/O interface 318 may be suitably comprised of one or more selected, conventional interface chips such as programmably interface adaptors (PIA's) which are available from Motorola, or programmable peripheral interfaces (PPI's) which are available from Intel. In the preferred embodiment, the I/O interface 318 is addressed like a peripheral in order to input and output control and data signals. This addressed I/O technique is well known to those skilled in the art and does not require further description herein. The I/O interface 318 receives as inputs the /SFF and /END signals from the data acquisition circuitry 230, a board in position BD IN POS, INDEXED and AIR pressure insufficient signals from sense switches 252, and 8-bit digital words from the data acquisition circuitry 230. The I/O interface 318 also outputs control signals from the microprocessor 312 to control the operation of the automated material classification apparatus. The I/O interface 318 outputs control signals to energize and de-energize the identification means 256, the pneumatic cylinder 73, the conveyor 14, and the hammer solenoid 82. In addition, the I/O interface 318 outputs ENAB and /READ signals from the microprocessor 312 to the data acquisition electronics 230.

After the computer 225 reads the preferred 575 digital sample words representing the data accelerometer 212 analog signal from the data acquisition RAM 260 into its own memory 316, it analyzes the data in a manner which is described in detail below. Generally, however, the first step in the analysis is to assign values from the stored data to a plurality of predetermined parameters or variables derived from predetermined characteristics of the sampled analog signal for a predetermined period, preferably over at least one cycle of the signal. The parameters are, at least initially, arbitrarily selected. However, experience has shown that the parameters which will now be identified provide highly accurate and repeatable calculations of the preferred MOE and MOR parameters for pre-cut lumber generally.

Figure 13:
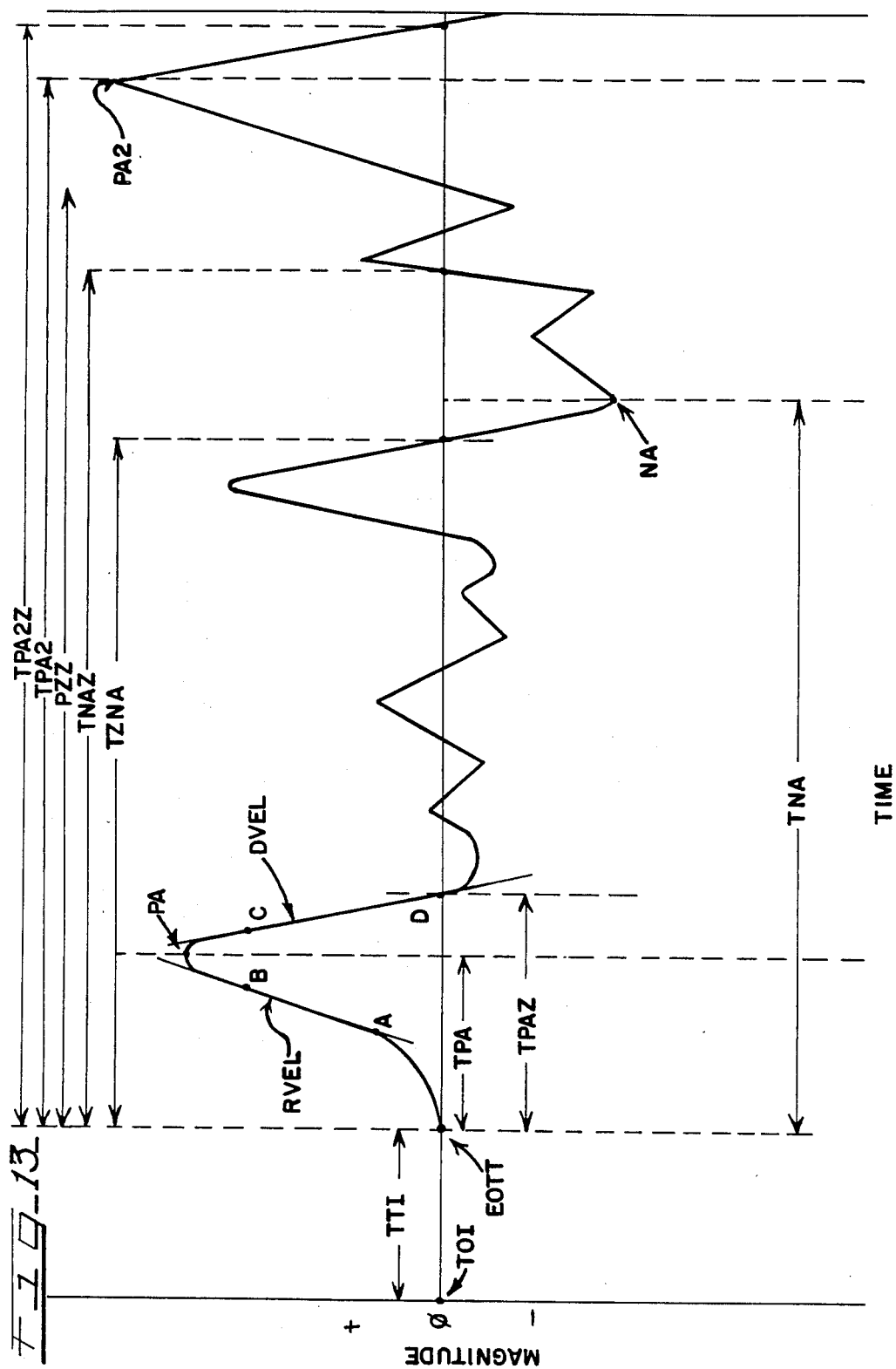
FIG. 13 is a graphical representation of one cycle of a typical signal generated by the preferred detector means of the apparatus corresponding to a compression force, showing a plurality of preferred parameters utilized by the preferred apparatus to characterize the signal.

FIG. 13 illustrates a typical analog waveform generated by the data accelerometer 212. The characteristics from which the parameters are derived are defined with respect to the waveform as follows. The time of impact TOI of the impactor means 75 against the board 16 is the point in time at which the data acquisition electronics 230 begins sampling the accelerometer signal. The end of transit time EOTT is the time when the accelerometer first detects the compression force generated as a result of the tap by the impactor means 75. This is the reference time used for all subsequent time measurements made of the sampled signal. The transit time interval TTI is the time interval from the time the impactor means 75 taps the board TOI to the end of transit time EOTT.

The first positive peak amplitude PA is the amplitude of the first positive peak that occurs in the waveform. The time of the first positive peak amplitude TPA is that time interval between the end of transit time EOTT and the occurrence of the first positive peak amplitude PA. The time of the first zero crossing after the occurrence of the first positive peak amplitude TPAZ is that time interval from the end of transit time EOTT to the occurrence of the first zero crossing after the occurrence of the first positive peak amplitude PA.

The second positive peak amplitude PA2 is the highest amplitude of the positive peak occurring between 300 and 575 time intervals (or samples). The time TPA2 to the second positive peak amplitude PA2 is that time interval from the end of transit time EOTT to the occurrence the second positive peak amplitude PA2. The time of the zero crossing immediately preceding the second positive peak amplitude PZZ is that time interval from the end of transit time EOTT to the occurrence of the zero crossing immediately preceding the second positive peak amplitude PA2. The time of the zero crossing immediately following the second positive peak amplitude TPA2Z is that time interval from the end of transit time EOTT to the occurrence of the first zero crossing after the occurrence of the second positive peak amplitude PA2.

The peak negative amplitude NA is the amplitude of the most negative point of the wave between the time of the first zero crossing after the first positive peak amplitude TPAZ and the time of the zero crossing immediately preceding the second positive peak amplitude PZZ. The time of the peak negative amplitude TNA is that time interval from the end of transit time EOTT to the occurrence of the peak negative amplitude NA. The time of the zero crossing immediately before the negative amplitude TZNA is that time interval from the end of transit time EOTT to the occurrence of the last zero crossing before the occurrence of the peak negative amplitude NA. The time of the zero crossing immediately after the occurrence of the peak negative amplitude TNAZ is that time interval between the end of transit time EOTT and the occurrence of the first zero crossing following the occurrence of the peak negative amplitude NA.

The average slope RVEL of the rising part of the first positive peak of the waveform is the slope between a selected point A on the waveform which in the preferred embodiment is one quarter of the amplitude of the first positive peak amplitude PA and a selected point B on the waveform which in the preferred embodiment is three quarters of the amplitude of the first positive peak amplitude PA. The average slope DVEL of the falling part of the first positive peak of the waveform is the slope between a selected point C on the waveform which in the preferred embodiment is three quarters of the amplitude of the peak amplitude PA and a selected point D on the waveform which in the preferred embodiment is the first zero crossing after the occurrence of the first positive peak amplitude PA.

The process by which the primary waveform characteristics are analyzed and used by the preferred classification apparatus to directly calculate the preferred MOE and MOR values for each individual board and to assign a corresponding grade classification thereto will now be described in detail. Referring to FIG. 14a, the apparatus initially goes through a setup process before actually grading any lumber. The computer 225 performs conventional initialization tasks at 500, 503. The computer then prompts the operator on the display terminal 228 to provide information such as nominal board size to be graded at 509, number of different grades for which to grade at 515, different parameters to grade for at 518, labels for each grade at 521, and upper and lower value limits for each grade at 524. The computer also instructs the operator to make any necessary mechanical adjustments, such as adjusting the positions of the carousel wheels 65a–c and the detector means 165, for the selected board size at 512.

After receiving the requested data, the computer waits for a terminal input at 530. Upon the occurrence of a terminal input, the terminal input is checked at 533 to see if it is a RUN command. If it is a RUN command, then the status of the grading portion of the apparatus is checked at 536. If the machine is already running then at 539 the computer ignores the input and continues operating where it left off when it received the RUN command. If the machine is not already running then at 542 the computer generates a control signal to energize the conveyor relay 248, updates, the display on the operator terminal 228, and initiates the grading process. If the terminal input is not a RUN command, then at 545 the computer issues a control signal to de-energize the conveyor relay and updates the operator terminal display accordingly. At 548 the computer determines if the terminal input is a STOP command. If the terminal input is a STOP command, then the computer waits for another terminal input at 530. If the terminal input is not a STOP command, then at 551, the computer checks the terminal input to see if it is a SET LIMITS command. If the terminal input is a SET LIMITS command, then the computer prompts the operator for upper and lower limits for each grade at 521 and continues on from that point. If the terminal input is not a SET LIMITS command and, then at 554 computer checks the terminal input to see if it is a SET GRADES command. If the terminal input is a SET GRADES command, then the computer system prompts the operator for labels for each grade at 521 and continues on from that point. If the terminal input is not a SET GRADES command, then at 557 the computer checks the terminal input to see if it is a QUIT command. If the terminal input is a QUIT command, then the microprocessor 312 of the computer enters a continuous loop at 560. If the terminal input is not a QUIT command, then the computer waits for another terminal input at 530.

Referring to FIG. 14b, when a RUN command is received, the computer reads the appropriate sense switch 252 to determine if there is a board in position to be graded at 563. If no board is in the grading position, then at 566 the computer checks for a pending operator terminal input. If there is a pending input, then the computer branches to the above-described terminal input routine at G. If a terminal input is not pending, then the computer checks again at 563 for a board in position to be graded. If a board is now in position to be graded, then at 569 the computer reads the air pressure sense switch 74 to determine if there is sufficient air pressure to operate the pneumatic cylinder 73 to clamp the board in place. If there is not enough air pressure to operate the pneumatic cylinder 73, then at 572 the computer generates a control signal to de-energize the conveyor relay 248 and halt the machine. The computer then informs the operator of the equipment failure on the operator terminal 228 and branches to wait for a terminal input at F. If there is sufficient air pressure to operate the pneumatic cylinder 73, then the computer generates a control signal to energize the pneumatic cylinder solenoid 250 to clamp the board into place at 575 and then enters a wait loop for approximately 320 milliseconds seconds at 578 to allow time for the clamping procedure to be completed. The computer then enables the data acquisition electronics 230 at 581 to sample the data accelerometer 212 analog signal upon the occurrence of a TRIGGER signal from the impact detector 148 by sending an ENAB signal thereto. The computer then generates a control signal at 584 to energize the relay 248 for the hammer solenoid 82 to impact the clamped board. The computer waits 25 milliseconds at 587 to allow time for the armature 92 of the solenoid 82 to overcome the tension in the armature thrust control spring 86 and impact the board 16. The computer then removes the control signal to de-energize the hammer solenoid 82 and removes the ENAB signal to disable the triggering portion of the data acquisition electronics 230 at 590 and starts an 18 millisecond timer at 593. The computer then checks at 596 for a low /END signal from the data acquisition electronics 230 indicating that data capture has been completed or if the timer has timed out at 599. If the apparatus is operating properly, data capture should be completed within 18 milliseconds as described above. If the timer has timed out and data capture has not been completed, then the computer recognizes that an error has occurred and at 602 informs the operator of the failure due to a faulty hammer solenoid on the operator terminal 228. If, however, data capture is completed before the timer times out, then the computer removes the pneumatic cylinder control signal to release the pneumatic cylinder 73 and unclamp the board in the grading position. The system's waveform variables identified above are then initialized at 608 and the computer begins analyzing the digital sample data generated by the detector means 165 and data acquisition circuitry 230.

The computer looks at the digital sample words in the data acquisition RAM 260 in chronological order at 611 and at 614 compares each sample with a selected threshold value, which in the preferred embodiment is approximately 0.219 volts. For each sample word examined, the transit time interval TTI is incremented by one unit at 620. The occurrence of eight consecutive samples above the threshold value indicates the start of reception by the data accelerometer 212 of the compression force resulting from the impact by the impactor means 75. The reception is treated as starting at the first of the eight consecutive samples. Once the computer finds eight consecutive samples greater than the threshold value at 617, it transfers 575 consecutive digital sample words to its own memory at 623, starting with the first of the eight consecutive data samples all greater than the threshold value. This point is defined as the end of transit time EOTT. At 626, the computer initializes the waveform variables described above relating to the first positive peak waveform. At 629-648, the computer examines the transferred data starting at the end of transit time EOTT and finds the sample which represents the amplitude of the first positive peak amplitude PA and stores the time from the end of transit time EOTT to the time that the first positive peak amplitude TPA occurred.

At 635-649, the computer also determines the first zero crossing following the occurrence of the first positive peak amplitude PA and stores the time TPAZ from the end of transit time EOTT to the occurrence of that first zero crossing. In addition, the computer updates a summation of the squares of the samples in the first positive peak waveform PSUMSQ at 641. The computer also updates the summation of the samples themselves PSUM and the count of the number of positive samples PCNT at 644.

Referring to FIG. 14c, upon the occurrence of the first zero crossing following the first peak amplitude PA, the computer increments the count of the number of positive passes PPASS by one at 650. The computer then examines the remaining samples in its memory at 653-686. In analyzing these samples, the computer counts the number of negative passes NPASS at 665 and positive passes PPASS at 650. The computer also determines the peak negative amplitude NA and the time from the end of transit time EOTT to the occurrence of the peak negative amplitude TNA at 677-683. In addition, at 659-663, the computer looks for the most positive peak PA2 occurring after the first positive peak amplitude PA and more than 300 samples after the end of transit time EOTT, and stores the time of this second peak amplitude TPA2, which is that time from the end of transit time EOTT to the occurrence o the second positive peak amplitude PA2. After examining all of the samples in its memory, the computer calculates the number of total periods NPP occurring in the sampled waveform at 682. Then, the computer determines the time interval from the end of transit time EOTT to the occurrence of the zero crossing immediately preceding the second peak amplitude PZZ at 695-710. Next, at 713-725 the computer determines the time TPA2Z from the end of transit time EOTT to the first zero crossing following the second positive peak amplitude, as long as the zero crossing occurs within the 575 samples in the computer's memory. This point is defined as identifying the end of one complete cycle of the signal or waveform. If a zero crossing after the second positive peak amplitude does not occur within 575 samples of the end of transit time EOTT, then the computer assigns a value of 575 to the parameter TPA2Z.

At 728-746, if the time of the peak negative amplitude TNA is greater than the time of the zero crossing immediately preceding the second positive peak amplitude PZZ then the computer discards the current values for the peak negative amplitude NA and the time of its occurrence TNA are discarded and replaced by the peak negative amplitude NA before the zero crossing immediately preceding the second positive peak amplitude PZZ. The computer then determines at 749-764 the time from the end of transit time EOTT to the zero crossing immediately preceding the peak negative amplitude NA before the time of the zero crossing immediately preceding the second positive peak amplitude TZNA.

Figure 14D:
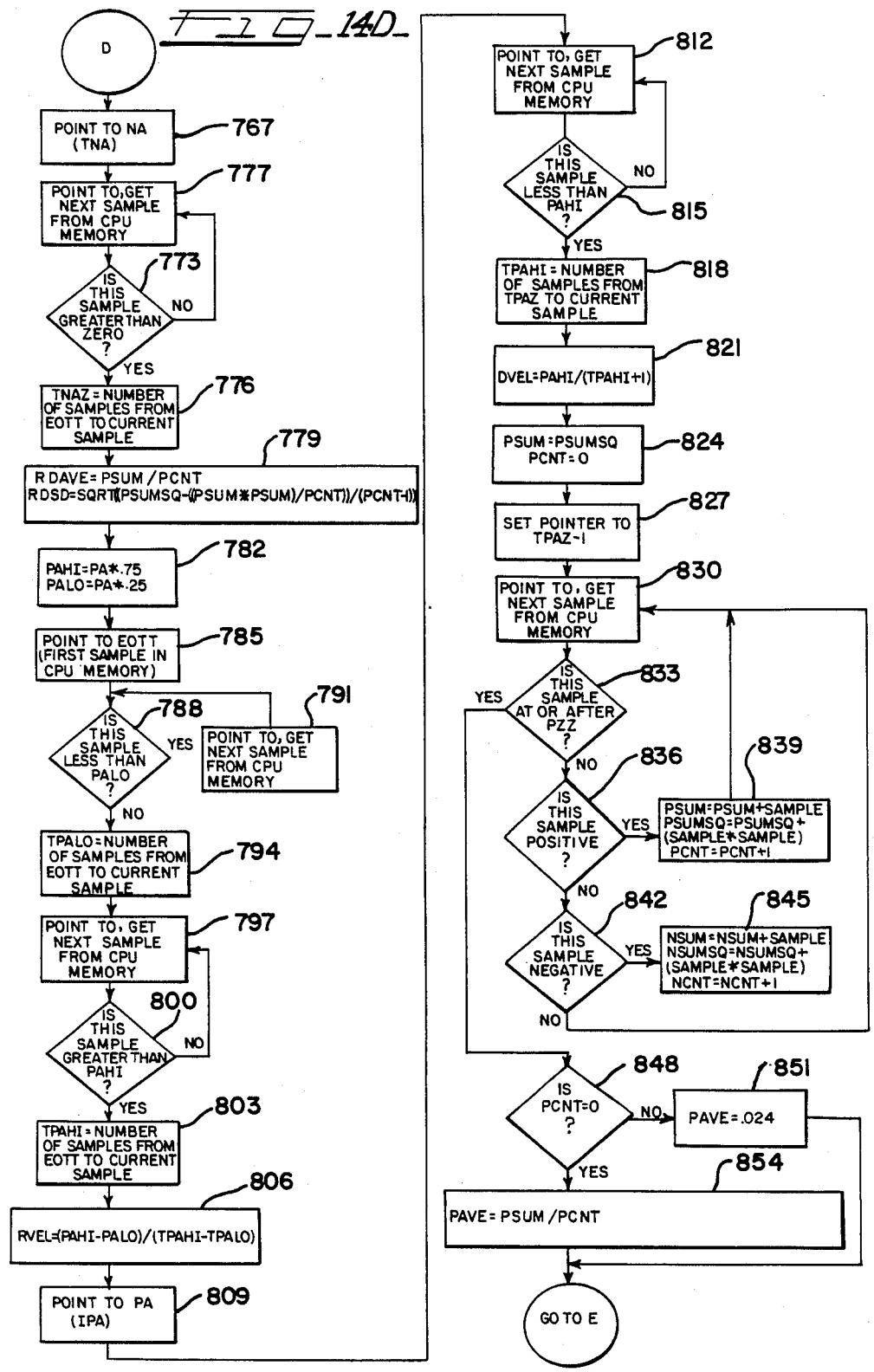

Referring to FIG. 14d, the computer next determines the time TNAZ from the end of transit time EOTT to the first zero crossing following the occurrence cf the peak negative amplitude NA at 767-776.

Based on the foregoing values, the computer next calculates a number of mathematical parameters. The average amplitude RDAVE of all positive amplitudes between the end of transit time EOTT and the time of the first zero crossing following the first positive peak amplitude TPAZ is calculated at 779. The standard deviation RDSD around that average amplitude RDAVE is also calculated at 779. Then the average slope RVEL of the rising portion of the waveform of the first positive peak is calculated at 782-806 and the slope of the descending portion DVEL of the first peak waveform is calculated at 809-821.

At 824, the computer sets the count of the number of positive samples PCNT, the summation of those samples PSUM, and the summation of the squares of those samples PSUMSQ equal to 0. At 827-845 the computer calculates the sum of and the sum of the squares of all positive amplitudes between the time TPAZ of the first zero crossing following the first positive peak amplitude PA and the time PZZ of the zero crossing immediately preceding the second positive peak amplitude PA2, as well as the sum of and the sum of the squares of all negative amplitudes during that time interval. At 849-855 the computer calculates the average value of the positive samples PAVE between the time TPAZ of the first zero crossing following the first positive peak amplitude PA and the time PZZ of the zero crossing immediately preceding the second positive peak amplitude PA2. If there are no positive samples in that time interval, then the computer sets the average PAVE equal to 0.024 at 860.

Referring to FIG. 14e, at 864 the computer calculates the standard deviation PSD around the average PAVE. If the number of positiVe samples is less than or equal to one, then the computer sets the standard deviation PSD equal to 0.001 at 858, 861. At 866-872, the computer calculates the standard deviation NSD around the average value of the negative samples between the time TPAZ of the first zero crossing following the first positive peak amplitude PA and the time PZZ of the zero crossing immediately preceding the second positive peak amplitude PA2. If the number of negative samples in that interval is one or less, then the computer sets the standard deviation NSD equal to 0.001 at 869. If there are no negative samples in that interval then the computer sets the average of the negative samples NAVE equal to 0.024 at 878, otherwise, the computer calculates the actual negative average NAVE at 881.

At this point, the computer has generated all of the preferred predetermined parameters describing the waveform. The computer next defines a preferred set of general variables (LEN, WIDTH, PAF, PA2F, X1-X32, SX1-SX32, IX1-IX32, ISX1-ISX32) at 884, 887 for use in one or more predetermined formulas corresponding to the particular lumber being graded and the selected parameters of interest. These general variables are, at least initially, arbitrarily determined by the user of the apparatus. However, experience has shown that the variables utilized in the preferred embodiments provide highly accurate and repeatable calculations of MOE and MOR in pre-cut lumber.

limits previously selected by the operator. The computer then assigns a grade value to each characteristic based on these comparisons.

```
    LEN  = length of the board (inches)
   WIDTH = width of the board (inches)
    PAF  = 125/(TPAZ-TPA)
    PA2F = 250/(TPAZ-PZZ)
     X1  = LEN/TTI                        SX1  = X1*X1
     X2  = TPA/100                        SX2  = X2*X2
     X3  = (TPAZ-TPA)/10                  SX3  = X3*X3
     X4  = PA * WIDTH/100                 SX4  = X4*X4
     X5  = 250/TPAZ                       SX5  = X5*X5
     X6  = (PZZ-TNA)/100                  SX6  = X6*X6
     X7  = TPAZ/(TPA2Z-PZZ)               SX7  = X7*X7
     X8  = ((TPAZ-TPA)*2)/(TPA2Z-PZZ)     SX8  = X8*X8
     X9  = PA2 * WIDTH/100                SX9  = X9*X9
    X10  = (TPA2-PZZ)/100                 SX10 = X10*X10
    X11  = 25/(TNAZ-TZNA)                 SX11 = X11*X11
    X12  = RDAVE * WIDTH/100              SX12 = X12*X12
    X13  = RDSD                           SX13 = X13*X13
    X14  = RVEL * WIDTH                   SX14 = X14*X14
    X15  = DVEL * WIDTH                   SX15 = X15*X15
    X16  = PZZ * (LENGTH/TTI)/100         SX16 = X16*X16
    X17  = (PAVE/RDAVE) * (PCNT/TPAZ)     SX17 = X17*X17
    X18  = (TPA2Z-TPA2)/10                SX18 = X18*X18
    X19  = NA * WIDTH * WIDTH/100         SX19 = X19*X19
    X20  = (TNA-TPA)/100                  SX20 = X20*X20
    X21  = PAVE * WIDTH/100               SX21 = X21*X21
    X22  = NAVE * WIDTH * WIDTH/100       SX22 = X22*X22
    X23  = PSD * WIDTH/10                 SX23 = X23*X23
    X24  = NSD * WIDTH/10                 SX24 = X24*X24
    X25  = PCNT/100                       SX25 = X25*X25
    X26  = NCNT/100                       SX26 = X26*X26
    X27  = ((PA2/PA)-1 * 1000/(TPA2-TPA)  SX27 = X27*X27
    X28  = PA2F/10                        SX28 = X28*X28
    X29  = (PAF+PA2F)/(PAF * PA2F)        SX29 = X29*X29
    X30  = (PAF-PA2F)/(PAF * PA2F))+1     SX30 = X30*X30
    X31  = (X5+PA2F)/(X5 * PA2F)          SX31 = X31*X31
    X32  = ((X5-PA2F)/(X5 * PA2F)+1       SX32 = X32*X32
    IX1  = 1/X1                           ISX1  = IX1*IX1
    IX2  = 1/X2                           ISX2  = IX2*IX2
    IX3  = 1/X3                           ISX3  = IX3*IX3
    IX4  = 1/X4                           ISX4  = IX4*IX4
    IX5  = 1/X5                           ISX5  = IX5*IX5
    IX6  = 1/X6                           ISX6  = IX6*IX6
    IX7  = 1/X7                           ISX7  = IX7*IX7
    IX8  = 1/X8                           ISX8  = IX8*IX8
    IX9  = 1/X9                           ISX9  = IX9*IX9
   IX10  = 1/X10                          ISX10 = IX10*IX10
   IX11  = 1/X11                          ISX11 = IX11*IX11
   IX12  = 1/X12                          ISX12 = IX12*IX12
   IX13  = 1/X13                          ISX13 = IX13*IX13
   IX14  = 1/X14                          ISX14 = IX14*IX14
   IX15  = 1/X15                          ISX15 = IX15*IX15
   IX16  = 1/X16                          ISX16 = IX16*IX16
   IX17  = 1/X17                          ISX17 = IX17*IX17
   IX18  = 1/X18                          ISX18 = IX18*IX18
   IX19  = 1/X19                          ISX19 = IX19*IX19
   IX20  = 1/X20                          ISX20 = IX20*IX20
   IX21  = 1/X21                          ISX21 = IX21*IX21
   IX22  = 1/X22                          ISX22 = IX22*IX22
   IX23  = 1/X23                          ISX23 = IX23*IX23
   IX24  = 1/X24                          ISX24 = IX24*IX24
   IX25  = 1/X25                          ISX25 = IX25*IX25
   IX26  = 1/X26                          ISX26 = IX26*IX26
   IX27  = 1/X27                          ISX27 = IX27*IX27
   IX28  = 1/X28                          ISX28 = IX28*IX28
   IX29  = 1/X29                          ISX29 = IX29*IX29
   IX30  = 1/X30                          ISX30 = IX30*IX30
   IX31  = 1/X31                          ISX31 = IX31*IX31
   IX32  = 1/X32                          ISX32 = IX32*IX32
```

The computer employs these general variables in one or more predetermined formulas, depending upon the lumber selected by the operator for grading and the selected physical parameters of interest, at 890-893 to calculate the selected physical parameters.

Referring to FIGS. 14f and 14g, the computer compares the calculated values of the selected physical characteristics of interest at 902-1001 with the grade limits previously selected by the operator. The computer then assigns a grade value to each characteristic based on these comparisons.

Referring to FIG. 14g, at 1106-1121, the computer assigns a final grade classification value to the piece of lumber graded. In the preferred embodiment, the final grade value corresponds to the lowest grade value assigned to any of the calculated parameters. At 1143-1149, the computer generates a control signal to energize the solenoid for the identification means 256 to mark the final grade in some identifiable form on the material tested. Alternatively or in addition thereto, the grade classification indicia may be displayed on the operator's terminal or another display means and the appropriate classification indicia applied manually. Next, the computer reads the appropriate sense switch 252 to determine if the board 16 is still in the grading position at 1155. If the board 16 is not in the grading position, then the computer branches to the beginning of the RUN routine at B. If the board 16 is still in the grading position, then the computer checks for a terminal input at 1158. If a terminal input is present then the computer branches to the terminal input routine at G. If a terminal input is not present, then the computer again checks to see if the board 16 is still in the grading position at 1155, and continues operation from there.

The predetermined formulas used to calculate the selected physical parameters of the board may vary depending on the type of lumber and the selected physical parameters to be calculated. In the preferred embodiment, the formulas are derived in several steps. First, a sample of the group of lumber of interest is subjected to impact analysis by the preferred lumber classification apparatus 10 as described above. In the preferred embodiment, highly accurate formulas have been dervied from the analysis of approximately 350 pieces of lumber, for example. However, a larger or smaller number of samples may be used as desired. In this initial step, the lumber classification apparatus stops its analysis once the general variables are calculated and does not calculate physical parameters or assign grade classifications to the boards.

In the next step of the process, the same lumber pieces are subjected to destructive testing to provide a preliminary set of estimates of the load-deflection ratio or slope (MOE) and the maximum load at failure (MOR) for each piece. As an example, for pre-cut boards, the destructive tests are preferably performed in accordance with ASTM Standard D-198, which is set out in the 1984 Annual Book of ASTM Standards, Section 4, Volume 4.09, preferably using the apparatus described at pgs. 110-111 thereof. Using the modulus of elasticity MOE and modulus of rupture MOR as selected characteristics, destructive, two-point load flexure tests are performed on each piece of sample lumber and the results of those tests are used to calculate sample estimates of MOE and MOR using the following formulas:

$$MOE = \frac{P'L^3}{4.7\,bh^3\Delta}$$

$$MOR = \frac{PL}{bh^2}$$

Where:
  $P'/\Delta$ is the load-deflection ratio or slope;
  L is the test span of the specimen between reaction supports;
  b is the dimension of the test specimen measured perpendicular to the load axis;
  h is the dimension of the test specimen measured parallel to the load axis;
  $\Delta$ is the deflection of the test specimen at the neutral axis and at the center of the span; and
  P is the maximum load on the test specimen at failure or rupture.

It is understood that other methods of obtaining estimated values for these and other physical characteristics are known in the art and could also be used. For example, different formulas would be used if the characteristics of interest were MOE and MOR in tension or compression rather than flexure.

In the next step, least squares multiple linear regressions are performed using all possible regressions and maximum $R^2$ procedures with the dependent variables being the general variables for which the classification apparatus obtained values from the samples and the independent variables being the sample estimates of MOE and MOR. The least squares multiple regression analysis is preferably performed with computer assistance. SAS Institute of Cary, N.C. offers a suitable statistical analysis program to perform least squares multiple linear regression analysis on the sample data called Statistical Analysis System SAS. Other regression analysis methods that are known in the art may also be used if desired.

Next, the variable values calculated by the preferred classification apparatus are inserted into the regression having the best $R^2$ value, i.e., the statistically optimum predictor of the estimated MOE and MOR variables, to generate predicted MOE and MOR values. The predicted MOE and MOR values and the corresponding MOE and MOR values derived from the destructive tests are then correlated to determine the statistical accuracy of the regression formula. In order to verify the prediction accuracy of the formula, some or all of the estimated values derived from the destructive test data may be varied within limits of acceptable error for the destructive test procedure used and which are well known in the art. This process is repeated until the regression formula is derived that accurately predicts MOE and MOR values derived from the destructive flexure test data and that provide acceptably high prediction accuracy based on a Predicted Residual Sum of Squares (PRSS) Statistical Analysis. The exemplary MOE and MOR formulas illustrated in FIG. 14e, for example, have been found to predict MOE and MOR values derived from destructive testing of southern pine two by fours and several other dimensions in flexure with $R^2$ and PRSS $R^2$ greater than 0.99.

What have been described are certain aspects of an automated lumber classification apparatus and method which constitutes a presently preferred embodiment of the invention. It is understood that the foregoing description and accompanying illustrations are merely exemplary and are not to be taken as limiting the scope of the invention, which is defined solely by the appended claims and their equivalents. Various changes and modifications to the preferred embodiment will be apparent to those skilled in the art. Such changes and modifications can be made without departing from the spirit and scope of the invention. Accordingly, it is intended that all such changes and modifications be covered by the appended claims and their equivalents.

I claim:

1. Automated material classification apparatus for material having a first end and a second end, said apparatus comprising:
  detector means for sensing an impact force and for providing a signal in response to the impact force;
  means for slidably supporting the material so that the material is freely movable relative to said detector means in one direction;

impactor means, located substantially at the first end of the material, for generating a force in the material in the one direction by impacting the material;

means locating said detector means substantially at the second end of the material, and generally opposite the first end of the material in the one direction, so that the detector means senses said impactor means force transmitted through the material and provides a signal related to said force;

computing means for assigning values to a selected plurality of predetermined parametrs characterizing said signal for at least one cycle thereof;

said computing means including means for processing said selected predetermined parameters according to at least one predetermined formula relating said parameters to at least one selected physical parameter of the material to generate at least one value signal corresponding to said at least one selected physical parameter; and identifying means for receiving said at least one value signal from said computing means and being operative to provide classification indicia associated with said at least one selected parameter of the material.

2. The automated material classification apparatus defined in claim 1 wherein said identifying means includes marking means for applying said classification indicia to said material.

3. The auotmated material classification apparatus defined in claim 1 wherein said impactor means includes means for impacting said material with a selectable predetermined force.

4. The automated material classification apparatus defined in claim 1 wherein said impactor means includes:

movable means for impacting said piece of material; and means for securely holding said piece of material in proximity to said movable means.

5. The automated material classification apparatus defined in claim 1 wherein said impactor means includes:

impacting means for applying an impact force to generate said compression force; and transmitter means located intermediate said impacting means and said material for receiving said impact force from said impacting means and transmitting it to said material.

6. The automated material classification apparatus defined in claim 5 wherein said transmitter means included means for contacting said material, said means being adapted to minimize the plastic zone between said material and said transmitter means.

7. The automated material classification apparatus defined in claim 1 including storage means for storing said signal related to said compression force for use by said computing means.

8. The automated material classification apparatus defined in claim 7 wherein said storage means comprises:

means for digitizing said signal at selected discrete time intervals to provide a plurality of digital words representing said signal; and memory means for storing said digital words.

9. The automated material classification apparatus defined in claim 1 wherein said computing means includes means connected to said impactor means for initiating operation of said impactor means in response to a predetermined condition.

10. The automated material classification apparatus defined in claim 9 wherein said means for initiating operation includes means responsive to the positioning of a piece of said material in a predetermined location proximal to said impactor means for initiating operation of said impactor means.

11. The automated material classification apparatus defined in claim 1 wherein said computing means includes means for selecting at least one said predetermined formula corresponding to a selected material from a plurality of predetermined formulas corresponding to a plurality of materials.

12. The automated material classification apparatus defined in claim 1 wherein said predetermined formula comprises an equation statistically derived from said predetermined parameters and said at least one selected physical parameter for a plurality of destructively tested pieces of said material.

13. The automated material classification apparatus defined in claim 12 wherein said equation is the statistically optimum predictor of the selected physical parameter of said material as a function of said selected predetermined parameters.

14. The automated material classification apparatus defined in claim 1 including means for supporting said material between said impactor means and said detector means, said impactor means being operative to impact a first surface of said material and said detector means being operative to provide a signal related to the compression force generated in said material at a second opposite surface thereof.

15. The automated material classification apparatus defined in claim 1 including material feeding means for automatically sequentially positioning individual pieces of said material between said impactor means and said detector means with a first surface of said material being adjacent to said impactor means and a second opposite surface being adjacent to said detector means.

16. The automated material classification apparatus defined in claim 15 wherein said material feeding means comprises:

rotatable carousel means having a plurality of spaced material receiving slots for holding a plurality of pieces of said material; and drive means for rotating said carousel incrementally so that each slot rotates sequentially between a material loading position, a material classification position between said impactor and said detector means, and a material unloading position.

17. A method of classifying a material having a first end and a second end, the method comprising the steps of:

slidably supporting the material so that the material is freely movable relative to detector means in one direction;

impacting a piece of the material with impacting means located substantially at the first end of the material, for generating a force in the material in the one direction by impacting the material;

in response to said impacting, providing a signal related to said force from said detector means located substantially at the second end of the material, and generally opposite the first end of the material in the one direction, so that the detector means senses said impactor means force transmitted through the material and provides a signal related to said force;

assigning values to a selected plurality of predetermined parameters characterizing said signal for at least one cycle thereof;

processing said selected predetermined parameters according to at least one predetermined formula relating said parameters to at least one selected physical parameter of the material to generate at least one value signal corresponding to said at least one selected physical parameter; and providing said at least one value signal to identifying means to cause said means to provide a classification indicia associated with said at least one selected physical parameter of the material.

18. The method defined in claim 17 wherein the step of providing said at least one value signal to said identifying means includes causing said identifying means to apply said classification indicia to said material.

19. The method defined in claim 17 wherein the step of impacting a piece of said material includes impacting said piece of material with a selectable predetermined force.

20. The method defined in claim 17 wherein the step of impacting a piece of said material includes the steps of:
securely holding said piece of material in proximity to movable means; and
impacting said piece of material with said movable means.

21. The method defined in claim 17 including the step of storing said signal for use in assigning said values.

22. The method defined in claim 21 wherein the step of storing said signal includes the steps of:
digitizing said signal at selected discrete time intervals to provide a plurality of digital words representing said signal; and
storing said digital words in memory means.

23. The method defined in claim 17 wherein the step of impacting said piece of material includes impacting said piece of material in response to a predetermined condition.

24. The method defined in claim 23 wherein said predetermined condition comprises said piece of material being positioned in a predetermined location proximal to said impactor means.

25. The method defined in claim 17 including the step of selecting at least one said predetermined formula corresponding to a selected material from a plurality of predetermined formulas corresponding to a plurality of materials.

26. The method defined in claim 17 wherein said predetermined formula comprises an equation statistically derived from said predetermined parameters and said at least one selected physical parameter for a plurality of destructively tested pieces of said material.

27. The method defined in claim 26 wherein said equation defines the statistically optimum predictor of said at least one selected physical parameter of said material as a function of said selected predetermined parameters.

28. The method defined in claim 27 including the steps of:
supporting said piece of material between said impacting means and said detecting means; and
operating said impactor means to impact a first surface of said piece of material and said detector means to provide a signal related to the compression force generated in said piece of material at a second opposite surface thereof.

29. The method defined in claim 17 including the step of:
automatically sequentially positioning individual pieces of said material between said impacting means and said detecting means with a first surface of said material being adjacent to said impacting means and a second opposite surface being adjacent to said detecting means.

30. Automated lumber classification apparatus comprising:
detector means for sensing an impact force and for providing a signal in response to the impact force;
means for slidably supporting a piece of lumber so that the piece of lumber is freely movable relative to said detector means in one direction;
impactor means, located substantially at a first end of the piece of lumber, for generating a force in the piece of lumber in the one direction by impacting the lumber;
means locating said detector means substantially at the second end of the piece of lumber, and generally opposite the first end of the piece of lumber in the one direction, so that the detector means senses said impactor means force transmitted through the piece of lumber and provides a signal related to said force;
computing means for assigning values to a selected plurality of predetermined parametrs characterizing said signal for at least one cycle thereof;
said computing means including means for processing said selected predetermined parameters according to at least one predetermined formula relating said parameters to at least one selected physical parameter of the piece of lumber to generate at least one value signal corresponding to said at least one selected physical parameter; and
identifying means for receiving said at least one value signal from said computing means and being operative to provide classification indicia associated with said at least one selected parameter of the piece of lumber.

31. The automated lumber classification apparatus defined in claim 30 wherein said identifying means includes marking means for applying said classification indicia to said lumber.

32. The automated lumber classification apparatus defined in claim 30 wherein said impactor means includes means for impacting said lumber with a selectable predetermined force.

33. The automated lumber classification apparatus defined in claim 30 wherein said impactor means includes:
movable means for impacting said piece of lumber; and
means for securely holding said piece of lumber in proximity to said movable means.

34. The automated lumber classification apparatus defined in claim 33 wherein said means for holding comprises means for holding said lumber longitudinally with an end thereof in proximity to said movable means.

35. The automated lumber classification apparatus defined in claim 30 wherein said impactor means includes:
impacting means for applying an impact force to generate said compression force; and
transmitter means located intermediate said impacting means and said lumber for receiving said impact force from said impacting means and transmitting it to said lumber.

36. The automated lumber classification apparatus defined in claim 35 wherein said transmitter means includes means for contacting said lumber, said means being adapted to minimize the plastic zone between said lumber and said transmitter means.

37. The automated lumber classification apparatus defined in claim 30 including storage means for storing said signal related to said compression force for use by said computing means.

38. The automated lumber classification apparatus defined in claim 33 wherein said storage means comprises:
means for digitizing said signal at selected discrete time intervals to provide a plurality of digital words representing said signal; and
memory means for storing said digital words.

39. The automated lumber classification apparatus defined in claim 30 wherein said computing means includes means connected to said impactor means for initiating operation of said impactor means in response to a predetermined condition.

40. The automated lumber classification apparatus defined in claim 39 wherein said means for initiating operation includes means responsive to the positioning of a piece of said lumber in a predetermined location proximal to said impactor means for initiating operation of said impactor means.

41. The automated lumber classification apparatus defined in claim 30 wherein said computing means includes means for selecting at least one said predetermined formula corresponding to a selected lumber type from a plurality of predetermined formulas corresponding to a plurality of selected lumber types.

42. The automated lumber classification apparatus defined in claim 30 wherein said predetermined formula comprises an equation statistically derived from said predetermined parameters and said at least one selected physical parameter for a plurality of destructively tested pieces of said lumber.

43. The automated lumber classification apparatus defined in claim 42 wherein said equation defines the statistically optimum predictor of said at least one selected physical parameter of said lumber as a function of said selected predetermined parameters.

44. The automated lumber classification apparatus defined in claim 30 including means for supporting said lumber between said impactor means and said detector means, said impactor means being operative to impact a first surface of said lumber and said detector means being operative to provide a signal related to the compression force generated in said lumber at a second opposite surface thereof.

45. The automated lumber classification apparatus defined in claim 44 wherein said means for supporting said lumber comprises means for supporting said lumber edgewise with a first longitudinal end thereof adjacent to said impactor means and a second opposite longitudinal end adjacent to said detector means.

46. The automated lumber classification apparatus defined in claim 30 including lumber feeding means for automatically sequentially positioning individual pieces of said lumber between said impactor means and said detector means with a first surface of said material being adjacent to said impactor means and a second opposite surface being adjacent to said detector means.

47. The automated lumber classification apparatus defined in claim 46 wherein said first surface comprises a first longitudinal end of said lumber and said second surface comprises a second opposite longitudinal end.

48. The automated lumber classification apparatus defined in claim 46 wherein said lumber feeding means comprises:
rotatable carousel means having a plurality of spaced lumber receiving slots for holding a plurality of pieces of said lumber edge-wise; and
drive means for rotating said carousel incrementally so that each slot rotates sequentially between a lumber loading position, a lumber classification position between said impactor and said detector means, and a lumber unloading position.

49. A method of classifying lumber having a first end and a second end, the method comprising the steps of:
slidably supporting the lumber so that the lumber is freely movable relative to detector means in one direction;
impacting a piece of the lumber with impacting means located substantially at the first end of the piece of lumber, for generating a force in the piece of lumber in the one direction by impacting the piece of lumber;
in response to said impacting, providing a signal related to said force from said detector means located substantially at the second end of the piece of lumber, and generally opposite the first end of the piece of lumber in the one direction, so that the detector means senses said impactor means force transmitted through the piece of lumber and provides a signal related to said force;
assigning values to a selected plurality of predetermined parameters characterizing said signal for at least one cycle thereof;
processing said selected predetermined parameters according to at least one predetermined formula relating said parameters to at least one selected physical parameter of the piece of lumber to generate at least one value signal signal for at least one selected physical parameter; and
providing said at least one value signal to identifying means to cause said means to provide a classification indicia associated with said at least one selected physical parameter of the piece of lumber.

50. The method defined in claim 49 wherein the step of providing said at least one value signal to said identifying means includes causing said identifying means to apply said classification indicia to said lumber.

51. The method defined in claim 49 wherein the step of impacting a piece of said lumber includes impacting said piece of lumber with a selectable predetermined force.

52. The method defined in claim 49 wherein the step of impacting a piece of said lumber includes the steps of:
securely holding said piece of lumber in proximity to movable means; and
impacting said piece of lumber with said movable means.

53. The method defined in claim 49 including the step of storing said signal for use in assigning said values.

54. The method defined in claim 53 wherein the step of storing said signal includes the steps of:
digitizing said signal at selected discrete time intervals to provide a plurality of digital words representing said signal; and
storing said digital words in memory means.

55. The method defined in claim 49 wherein the step of impacting said piece of lumber includes impacting said piece of lumber in response to a predetermined condition.

56. The method defined in claim 55 wherein the step of impacting said piece of lumber includes impacting said piece of lumber when said piece of lumber is positioned in a predetermined location proximal to said impactor means.

57. The method defined in claim 49 including the step of selecting at least one said predetermined formula corresponding to a selected lumber type from a plurality of predetermined formulas corresponding to a plurality of lumber types.

58. The method defined in claim 49 wherein said predetermined formula comprises an equation statistically derived from said predetermined parameters and said at least one selected physical parameter for a plurality of destructively tested pieces of said lumber.

59. The method defined in claim 58 wherein said equation defines the statistically optimum predictor of said at least one selected physical parameter of said lumber as a function of said selected predetermined parameters.

60. The method defined in claim 49 including the steps of:
supporting said piece of lumber between said impacting means and said detecting means; and
operating said impactor means to impact a first surface of said piece of lumber and said detector means to provide a signal related to the compression force generated in said piece of lumber at a second opposite surface thereof.

61. The method defined in claim 60 wherein supporting said piece of lumber includes supporting said piece of lumber edgewise with a first longitudinal end adjacent to said impactor means and a second opposite longitudinal end adjacent to said detector means.

62. The method defined in claim 60 wherein said first surface comprises a first longitudinal end of said lumber and said second surface comprises a second opposite longitudinal end of said lumber.

63. The method defined in claim 49 including the step of:
automatically sequentially positioning individual pieces of said lumber between said impacting means and said detecting means with a first surface of said lumber being adjacent to said impacting means and a second opposite surface being adjacent to said detecting means.

64. The method defined in claim 63 wherein said first surface comprises a first longitudinal end of said lumber and said second surface comprises a second opposite longitudinal end of said lumber.

65. The method defined in claim 49 further comprising the step of:
isolating said piece of material from mechanical vibration before said impacting means impacts said piece of lumber.

66. A lumber feeding apparatus, comprising:
rotatable lumber receiving means comprising a drive shaft and a plurality of carousel wheels mounted on said drive shaft in spaced relation, each one of said carousel wheels including a corresponding plurality of compartments aligned for receiving at least one piece of lumber and means for isolating said at least one piece of lumber from mechanical vibrations;
conveyor means for continuously transporting a plurality of pieces of lumber to said lumber receiving means;
means for restraining said plurality of pieces of lumber on said conveyor means;
means for selectively releasing said restraining means to allow a selected number of pieces of lumber to be transported to said lumber receiving means; and
means for rotating said lumber receiving means after said lumber receiving means receives said selected number of pieces of lumber so that said selected number of pieces are rotated to a processing position.

* * * * *

UNITED STATES PATENT AND TRADEMARK OFFICE
CERTIFICATE OF CORRECTION

PATENT NO. : 4,852,029

DATED : July 25, 1989

INVENTOR(S) : Thomas A. Pope, deceased, et al.

It is certified that error appears in the above-identified patent and that said Letters Patent is hereby corrected as shown below:

ON THE TITLE PAGE,
IN OTHER PUBLICATIONS

On page 2, column 2, after "(Logan)." please insert --_Dynamic Modulus of Elasticity and Pulse Constant of Wood by Pulse Transmission Technique_, Journal of the T.D.A., pp. 19-24 (Sekhar).
_Non-Destructive Testing of Timber at Washington State University_, Conference on Non-Destructive Testing of Concrete and Timber, pp. 53-58 (Pellerin).
_Measurement of Elasticity of Lumber with Longitudinal Stress Wave and the Piezoelectric Effect of Wood_, pp. 223-244 (Galligan et al.).
_Factors for Consideration in Planning for an MSR Grading Operation_, Proceedings of Third Short Course on Machine Stress-Rated Lumber (Galligan).
_Commercial Grading Machines_, Proceedings of Third Short Course of Machine Stress-Rated Lumber (Knudson).
_Stress Grade Analysis System from Accu-Tech, Inc._, 1982.--

UNITED STATES PATENT AND TRADEMARK OFFICE
CERTIFICATE OF CORRECTION

PATENT NO. : 4,852,029

DATED : July 25, 1989

INVENTOR(S) : Thomas A. Pope, deceased, et al.

It is certified that error appears in the above-identified patent and that said Letters Patent is hereby corrected as shown below:

In column 4, line 68, please delete "longitudional" and substitute therefor --longitudinal--.

In column 9, lines 32 and 33, please delete "reciving" and substitute therefor --receiving--.

In column 12, line 63, please delete "bolt" and substitute therefor --bolts--.

In column 17, lines 65 and 66, please delete "cylindrical 71 rod" and substitute therefor --horizontal rod 71--.

In column 19, line 2, please delete "correspondig" and substitute therefor --corresponding--.

In column 25, line 42, after "updates" please delete --;--.

In column 25, line 57, please delete "and".

In column 26, line 25, please delete "seconds".

In column 27, line 43, please delete "o" and substitute therefor --of--.

In column 28, line 27, after "calculates" please delete "the sum of and".

UNITED STATES PATENT AND TRADEMARK OFFICE
CERTIFICATE OF CORRECTION

PATENT NO. : 4,852,029

DATED : July 25, 1989

INVENTOR(S) : Thomas A. Pope, deceased, et al.

It is certified that error appears in the above-identified patent and that said Letters Patent is hereby corrected as shown below:

In column 28, line 32, after the first occurrence of "sum of" please delete "and the sum of".

In column 28, line 44, please delete "positiVe" and substitute therefor --positive--.

In column 32, line 66, please delete "support:ing" and substitute therefor --supporting--.

IN THE CLAIMS

In claim 49, column 38, line 41, after "for" please insert --said--.

In claim 66, column 40, line 35, after "of" please insert --said--.

Signed and Sealed this

Twenty-eighth Day of July, 1992

Attest:

DOUGLAS B. COMER

*Attesting Officer*     *Acting Commissioner of Patents and Trademarks*